(12) United States Patent
Adler et al.

(10) Patent No.: US 7,588,535 B2
(45) Date of Patent: Sep. 15, 2009

(54) APPARATUS, METHOD AND SYSTEM FOR INTRAVASCULAR PHOTOGRAPHIC IMAGING

(75) Inventors: Doron Adler, Nesher (IL); Alex Zaretski, Nesher (IL); Ofer Pillar, Kirvat Haim (IL); Keren Shafrir, Haifa (IL); Mordechai Segev, Ramat Alon (IL)

(73) Assignee: C2Cure Inc., Wilmington, DE (US)

( * ) Notice: Subject to any disclaimer, the term of this patent is extended or adjusted under 35 U.S.C. 154(b) by 664 days.

(21) Appl. No.: 10/498,150

(22) PCT Filed: Dec. 11, 2002

(86) PCT No.: PCT/IL02/00999

§ 371 (c)(1),
(2), (4) Date: Feb. 25, 2005

(87) PCT Pub. No.: WO03/053226

PCT Pub. Date: Jul. 3, 2003

(65) Prior Publication Data

US 2005/0165279 A1    Jul. 28, 2005

(51) Int. Cl.
*A61B 1/04* (2006.01)
*A61B 6/00* (2006.01)

(52) U.S. Cl. ............... 600/109; 600/178; 600/181; 600/160; 600/476; 600/477

(58) Field of Classification Search ........... 600/109, 600/160, 178, 181, 476–478
See application file for complete search history.

(56) References Cited

U.S. PATENT DOCUMENTS

| 3,321,656 A | * | 5/1967 | Sheldon ............ 313/385 |
| 3,971,065 A | | 7/1976 | Bayer |
| 4,253,447 A | | 3/1981 | Moore et al. |
| 4,261,344 A | | 4/1981 | Moore et al. |
| 4,467,361 A | | 8/1984 | Ohno et al. |
| 4,491,865 A | | 1/1985 | Danna et al. |
| 4,555,768 A | | 11/1985 | Lewis et al. |
| 4,569,335 A | | 2/1986 | Tsuno |

(Continued)

FOREIGN PATENT DOCUMENTS

DE    3529026    2/1986

(Continued)

OTHER PUBLICATIONS

"A Review of the Optical Properties of Biological Tissues", Cheong, Prahl and Welch, IEEE J. of Quantum Electronics, vol. 26, Dec. 12, 1990.

(Continued)

*Primary Examiner*—John P Leubecker
(74) *Attorney, Agent, or Firm*—Ganz Law, P.C.

(57) ABSTRACT

An apparatus, system and method for providing an image enhancing effect for a photographic image of a target region within an intravascular environment. The image enhancing effects may be a physical process based upon the nature of the detected light or based upon different aspects of expected light reflection behavior, for example, by running predefined image reconstruction algorithms. The apparatus has a plurality of different embodiments, each of which reduces the ambient "noise" detected along with the light reflected from the target region in order to increase the signal/noise ratio, thereby to enhance the quality of the image produced.

58 Claims, 8 Drawing Sheets

U.S. PATENT DOCUMENTS

| | | | |
|---|---|---|---|
| 4,573,450 A | 3/1986 | Arakawa | |
| 4,576,146 A | 3/1986 | Kawazoe et al. | |
| 4,602,281 A * | 7/1986 | Nagasaki et al. | 348/69 |
| 4,604,992 A | 8/1986 | Sato | |
| 4,625,236 A | 11/1986 | Fujimori et al. | |
| 4,633,304 A | 12/1986 | Nagasaki | |
| 4,646,721 A | 3/1987 | Arakawa | |
| 4,651,201 A | 3/1987 | Schoolman | |
| 4,682,219 A | 7/1987 | Arakawa et al. | |
| 4,692,608 A | 9/1987 | Cooper et al. | |
| 4,697,208 A | 9/1987 | Eino | |
| 4,713,683 A | 12/1987 | Fujimori et al. | |
| 4,714,319 A | 12/1987 | Zeevi et al. | |
| 4,720,178 A | 1/1988 | Nishioka et al. | |
| 4,746,203 A | 5/1988 | Nishioka et al. | |
| 4,757,805 A | 7/1988 | Yabe | |
| 4,768,513 A * | 9/1988 | Suzuki | 600/476 |
| 4,784,133 A | 11/1988 | Mackin | |
| 4,803,550 A * | 2/1989 | Yabe et al. | 348/68 |
| 4,803,562 A | 2/1989 | Eino | |
| 4,809,680 A | 3/1989 | Yabe | |
| 4,819,065 A | 4/1989 | Eino | |
| 4,827,907 A * | 5/1989 | Tashiro | 600/109 |
| 4,831,456 A | 5/1989 | Takamura | |
| 4,832,003 A | 5/1989 | Yabe | |
| 4,832,033 A | 5/1989 | Maher et al. | |
| 4,857,724 A | 8/1989 | Snoeren | |
| 4,866,526 A | 9/1989 | Ams et al. | |
| 4,869,256 A | 9/1989 | Kanno et al. | |
| 4,884,133 A | 11/1989 | Kanno et al. | |
| 4,905,670 A | 3/1990 | Adair | |
| 4,926,257 A | 5/1990 | Miyazaki | |
| 4,934,339 A | 6/1990 | Kato | |
| 4,939,573 A | 7/1990 | Teranishi et al. | |
| 4,953,539 A | 9/1990 | Nakamura et al. | |
| 4,967,269 A | 10/1990 | Sasagawa et al. | |
| 4,986,642 A | 1/1991 | Yokota et al. | |
| 4,998,972 A * | 3/1991 | Chin et al. | 600/109 |
| 5,010,875 A | 4/1991 | Kato | |
| 5,021,888 A | 6/1991 | Kondou et al. | |
| 5,022,399 A | 6/1991 | Biegeleisen | |
| 5,029,574 A | 7/1991 | Shimamura et al. | |
| 5,122,650 A | 6/1992 | McKinley | |
| 5,166,787 A | 11/1992 | Irion | |
| 5,184,223 A | 2/1993 | Mihara | |
| 5,191,203 A | 3/1993 | McKinley | |
| 5,216,512 A | 6/1993 | Bruijns et al. | |
| 5,222,477 A | 6/1993 | Lia | |
| 5,264,925 A | 11/1993 | Shipp et al. | |
| 5,301,090 A | 4/1994 | Hed | |
| 5,311,600 A | 5/1994 | Aghajan et al. | |
| 5,323,233 A | 6/1994 | Yamagami et al. | |
| 5,325,847 A | 7/1994 | Matsuno | |
| 5,335,662 A | 8/1994 | Kimura et al. | |
| 5,343,254 A | 8/1994 | Wada et al. | |
| 5,376,960 A | 12/1994 | Wurster | |
| 5,408,268 A | 4/1995 | Shipp | |
| 5,432,543 A | 7/1995 | Hasegawa et al. | |
| 5,444,574 A | 8/1995 | Ono et al. | |
| 5,450,243 A | 9/1995 | Nishioka | |
| 5,471,237 A | 11/1995 | Shipp | |
| 5,494,483 A | 2/1996 | Adair | |
| 5,498,230 A | 3/1996 | Adair | |
| 5,512,940 A | 4/1996 | Takasugi et al. | |
| 5,547,455 A | 8/1996 | McKenna et al. | |
| 5,557,324 A * | 9/1996 | Wolff | 345/207 |
| 5,575,754 A | 11/1996 | Konumura | |
| 5,594,497 A | 1/1997 | Ahern et al. | |
| 5,598,205 A | 1/1997 | Nishioka | |
| 5,603,687 A | 2/1997 | Hori et al. | |
| 5,673,147 A | 9/1997 | McKinley | |
| 5,700,236 A | 12/1997 | Sauer et al. | |
| 5,712,493 A | 1/1998 | Mori et al. | |
| 5,728,044 A | 3/1998 | Shan | |
| 5,751,341 A | 5/1998 | Chaleki et al. | |
| 5,792,045 A | 8/1998 | Adair | |
| 5,797,837 A | 8/1998 | Minami | |
| 5,847,394 A * | 12/1998 | Alfano et al. | 250/341.8 |
| 5,905,597 A | 5/1999 | Mizouchi et al. | |
| 5,907,178 A | 5/1999 | Baker et al. | |
| 5,928,137 A | 7/1999 | Green | |
| 5,929,901 A | 7/1999 | Adair et al. | |
| 5,940,126 A | 8/1999 | Kimura | |
| 5,944,655 A | 8/1999 | Becker | |
| 5,984,860 A | 11/1999 | Shan | |
| 5,986,693 A | 11/1999 | Adair et al. | |
| 6,001,084 A | 12/1999 | Rick et al. | |
| 6,009,189 A | 12/1999 | Schaack | |
| 6,010,449 A | 1/2000 | Selmon et al. | |
| 6,039,693 A | 3/2000 | Seward et al. | |
| 6,043,839 A | 3/2000 | Adair et al. | |
| 6,075,235 A * | 6/2000 | Chun | 250/208.1 |
| 6,099,475 A | 8/2000 | Seward et al. | |
| 6,129,672 A | 10/2000 | Seward et al. | |
| 6,134,003 A | 10/2000 | Tearney et al. | |
| 6,139,490 A | 10/2000 | Breidenthal et al. | |
| 6,142,930 A | 11/2000 | Ito et al. | |
| 6,148,227 A | 11/2000 | Wagnieres et al. | |
| 6,177,984 B1 * | 1/2001 | Jacques | 356/39 |
| 6,178,346 B1 * | 1/2001 | Amundson et al. | 600/473 |
| 6,184,923 B1 | 2/2001 | Miyazaki | |
| 6,206,825 B1 | 3/2001 | Tsuyuki | |
| 6,240,312 B1 | 5/2001 | Alfano et al. | |
| 6,281,506 B1 | 8/2001 | Fujita et al. | |
| 6,327,374 B1 | 12/2001 | Piironen et al. | |
| 6,331,156 B1 | 12/2001 | Haefele et al. | |
| 6,416,463 B1 | 7/2002 | Tsuzuki et al. | |
| 6,449,006 B1 | 9/2002 | Shipp | |
| 6,459,919 B1 | 10/2002 | Lys et al. | |
| 6,464,633 B1 | 10/2002 | Hosoda et al. | |
| 6,476,851 B1 | 11/2002 | Nakamura | |
| 6,485,414 B1 | 11/2002 | Neuberger | |
| 6,533,722 B2 | 3/2003 | Nakashima | |
| 6,659,940 B2 | 12/2003 | Adler | |
| 6,670,636 B2 | 12/2003 | Hayashi et al. | |
| 6,692,430 B2 | 2/2004 | Adler | |
| 6,697,110 B1 | 2/2004 | Jaspers et al. | |
| 6,943,837 B1 | 9/2005 | Booth, Jr. | |
| 6,984,205 B2 | 1/2006 | Gazdzinski | |
| 7,123,301 B1 | 10/2006 | Nakamura et al. | |
| 7,127,280 B2 * | 10/2006 | Dauga | 600/407 |
| 7,133,073 B1 | 11/2006 | Neter | |
| 7,241,262 B2 | 7/2007 | Adler et al. | |
| 7,308,296 B2 | 12/2007 | Lys et al. | |
| 7,347,817 B2 * | 3/2008 | Glukhovsky et al. | 600/181 |
| 7,355,625 B1 | 4/2008 | Mochida et al. | |
| 2001/0031912 A1 | 10/2001 | Adler | |
| 2001/0040211 A1 | 11/2001 | Nagaoka | |
| 2001/0051766 A1 | 12/2001 | Gazdzinski | |
| 2002/0089586 A1 | 7/2002 | Suzuki et al. | |
| 2003/0174409 A1 | 9/2003 | Nagaoka | |
| 2004/0019255 A1 | 1/2004 | Sakiyama | |
| 2005/0259487 A1 | 11/2005 | Glukhovsky et al. | |
| 2006/0158512 A1 | 7/2006 | Iddan et al. | |
| 2006/0183976 A1 | 8/2006 | Adler et al. | |
| 2007/0100241 A1 | 5/2007 | Adler | |

FOREIGN PATENT DOCUMENTS

| | | |
|---|---|---|
| DE | 3720624 | 1/1989 |
| DE | 19800312 | 7/1999 |
| EP | 0630056 A1 | 12/1994 |
| EP | 434793 B1 | 4/1995 |
| EP | 0827908 A1 | 3/1998 |

| | | |
|---|---|---|
| JP | 60258515 | 5/1985 |
| JP | 60104915 | 6/1985 |
| JP | 61018915 A | 1/1986 |
| JP | 63244011 A | 3/1987 |
| JP | 3264043 A | 11/1991 |
| JP | 4236934 A | 8/1992 |
| JP | 5307144 | 11/1993 |
| JP | 06222283 A2 | 12/1993 |
| JP | 7163517 A | 12/1993 |
| JP | 8220448 A | 2/1995 |
| JP | 7318815 A | 6/1995 |
| JP | 8024219 A | 1/1996 |
| JP | 8082751 A | 3/1996 |
| JP | 8114755 A | 5/1996 |
| JP | 11019026 | 1/1999 |
| JP | 2006198424 | 3/2006 |
| WO | WO9715229 A1 | 5/1997 |
| WO | WO/9732534 A1 | 9/1997 |
| WO | WO99/23812 A2 | 11/1998 |
| WO | WO99/60916 | 2/1999 |
| WO | WO0045691 | 8/2000 |
| WO | WO0122741 A2 | 3/2001 |
| WO | WO /0176452 | 10/2001 |
| WO | WO03013624 A2 | 2/2003 |
| WO | WO2003/098913 A3 | 5/2003 |

OTHER PUBLICATIONS

"Optical Properties of Circulating Human Blood in Wavelength Range 400-2500 nm" Andre Roggan, Journal of Biomedical Optics, Jan. 1999.

English Abstract of Japan of JP 08114755 dated May 7, 1996.

English Abstract of Japan of JP 08024219 dated Jan. 30, 1996.

European Examination Report for European Application No. 01919745.8, dated Jul. 20, 2006, EPO, 4 pages.

PCT International Search Report dated Oct. 21, 2001, for corresponding PCT International Application No. PCT/IL01/00313, filed Apr. 4, 2001, 3 pages.

PCT International Search Report dated Jul. 9, 2004, for corresponding PCT International Application No. PCT/US03/32975, filed Oct. 17, 2003.

Fujipoly America Corp—General Information; http//www.fujipoly.com/general/default.asp; accessed Jun. 11, 2004.

PCT International Search Report dated Mar. 24, 2004, for corresponding PCT International Application No. PCT/IL03/00399, filed May 15, 2003.

Fujipoly America Corp—Zebra Elastomeric Connectors, http://www.fujipoly.com/products/genProductLine.asp?Productline=zebra; accessed Jun. 11, 2004.

European Examination Report for related European patent application No. 01919745.8, dated Nov. 28, 2007, 2 pages.

United States Patent and Trademark Office Action dated Aug. 9, 2006 for U.S. Appl. No. 10/759,045, filed Jan. 20, 2004, 9 pages.

Final Office Action for co-pending U.S. Appl. No. 11/298,265, dated Oct. 16, 2008.

Office Action dated Dec. 1, 2008 for related Israel Patent Application No. 162420 (in the Hebrew language); 3 pages.

International PCT Search Report dated Jun. 10, 2004 for related International patent application No. PCT/ IL02/00659, filed Aug. 11, 2002; 1 page.

European Search Report dated Nov. 26, 2008 for related European patent application No. EP02758761, filed Aug. 11, 2002; 6 pages.

MIZUNO, K. et al. "New Percutaneous Transluminal Coronary Angioscope" Selected papers on optical fibers in Medicine; SPIE Milestone Series; Bellingham, SPIE, US, vol. MS 11, Jan. 1, 1990 pp. 150-155.

Office Action for co-pending U.S. Appl. No. 11/298,265, dated Apr 2, 2008.

European Examination Report for corresponding European patent application No. 02795407.2 dated Apr. 23, 2009; 4 pages.

Supplementary European Search Report dated Dec. 22, 2008 for corresponding European patent application No. 02795407.2; 4 pages.

* cited by examiner

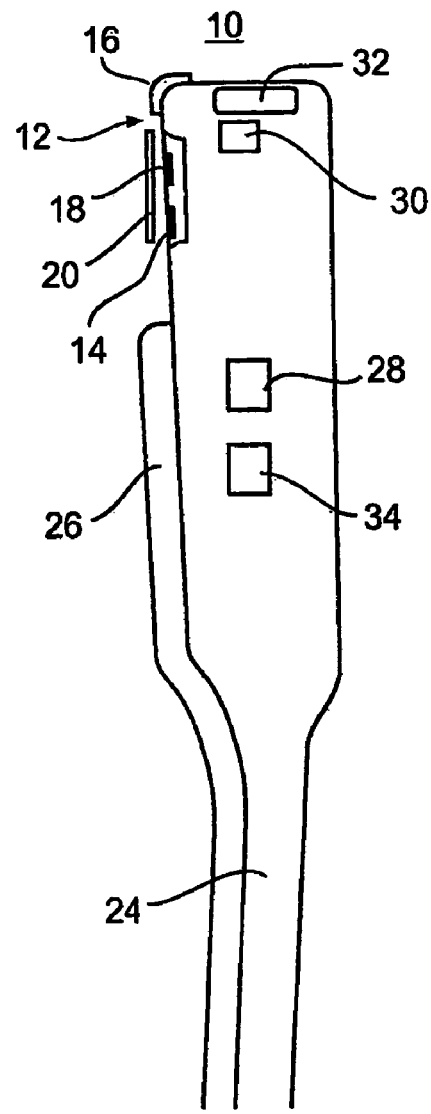
Fig. 1
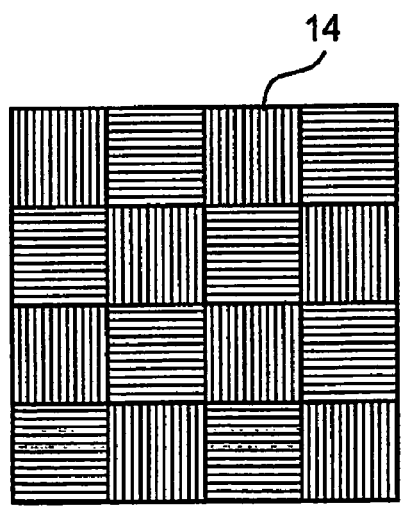
Fig. 2
| A | B | A | B |
|---|---|---|---|
| B | A | B | A |
| A | B | A | B |
| B | A | B | A |
Fig. 3

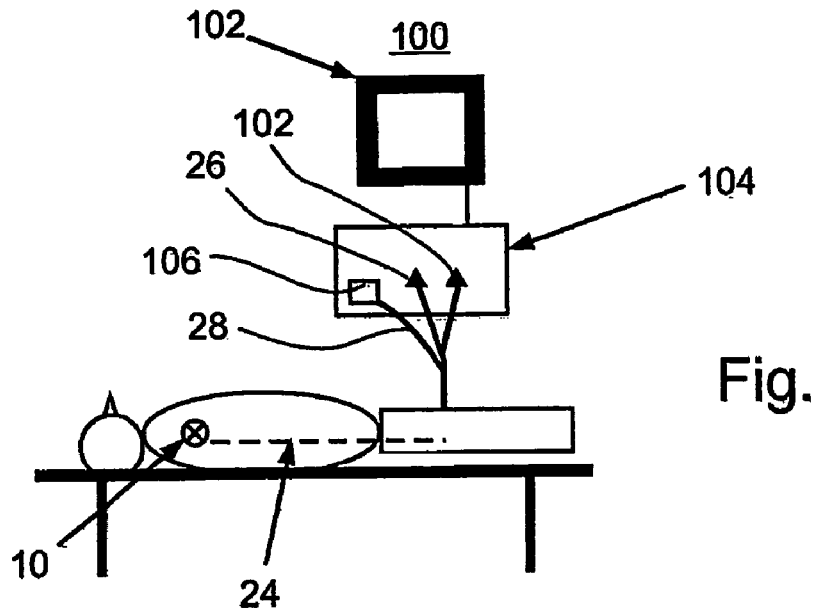
Fig. 11
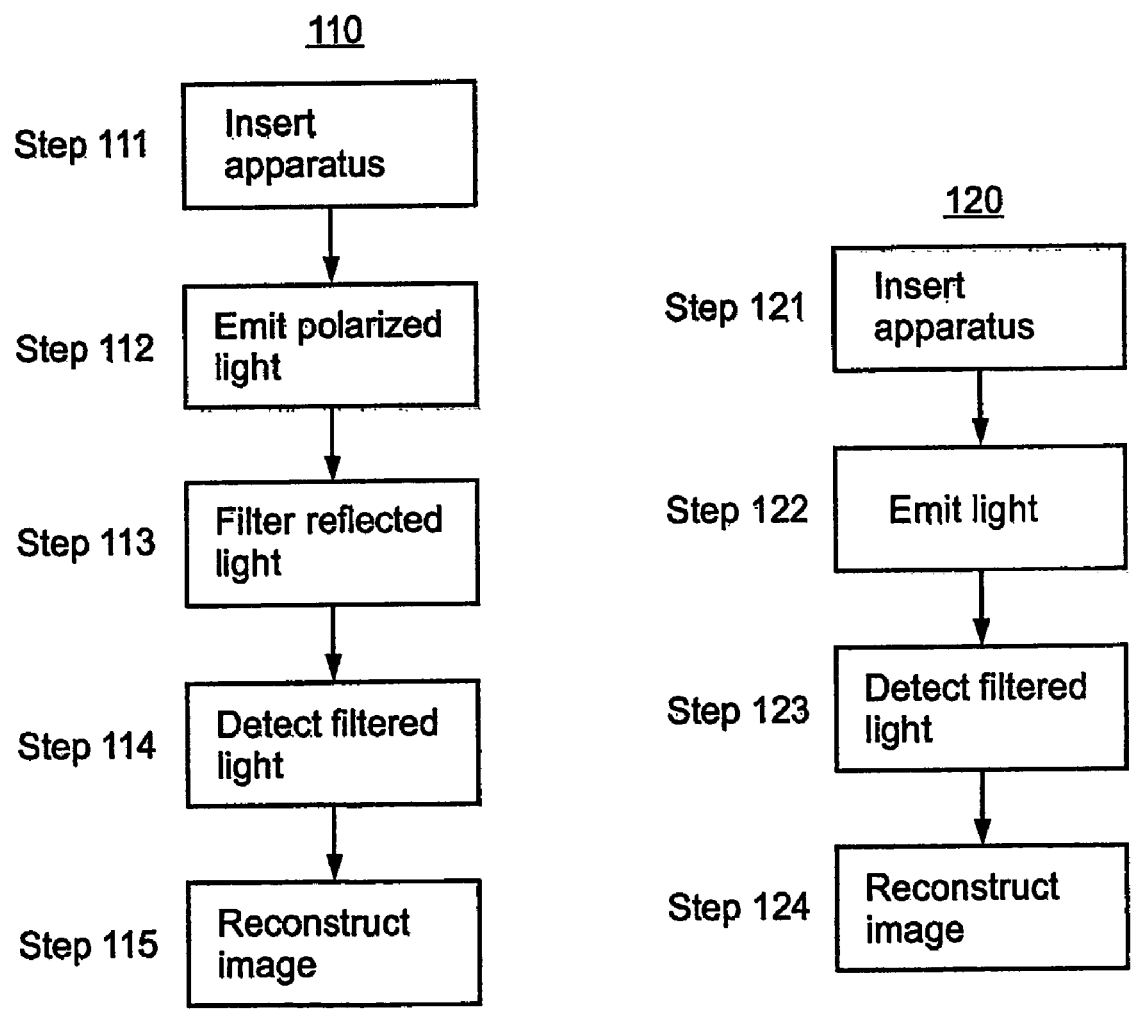
Fig. 12
Fig. 13

APPARATUS, METHOD AND SYSTEM FOR INTRAVASCULAR PHOTOGRAPHIC IMAGING

FIELD AND BACKGROUND OF THE INVENTION

The present invention relates to imaging and, more particularly, to an apparatus, system and method for imaging within an intravascular environment, especially of vascular walls.

Endoscopic surgery, which involves the use of an imaging device to see images of the body's internal structures, has been used for decades in many different diagnostic and surgical procedures, including gall bladder removal, tubal ligation, and knee surgery. Recently, such methods have become widely used in plastic surgery, including both cosmetic and re-constructive procedures. The use of the imaging device allows such surgery to be performed in a minimally invasive manner.

An endoscope is a rigid or flexible optical instrument which comprises a tubular probe containing a small camera head, a camera control unit, a light source and a transmission cable. The endoscope is inserted through a small incision in the body and is moved to the viewing site in order to provide an image of the object of interest. The endoscope is connected to a viewing screen which magnifies the transmitted images of the object. During surgery, the surgeon is able to view the surgical area by watching the screen while moving the tube of the endoscope through the surgical area.

Endoscopy has limited application because most current endoscopes provide only flat, two-dimensional images which are not always sufficient for the requirements of precise diagnosis or treatment. There have been many attempts in the past to overcome this limitation, particularly by providing for three dimensional imaging. For example, providing stereoscopic images of an object by using two different optical paths is disclosed in a number of patents, including U.S. Pat. Nos. 5,944,655; 5,222,477; 4,651,201; 5,191,203; 5,122,650; 5,471,237; 5,673,147; 6,139,490 and 5,603,687. Further attempts to obtain a three dimensional image are disclosed in U.S. Pat. No. 4,714,319 in which two light sources are used to give an illusion of a stereoscopic image based upon shadows and in Japan Patent No. 131,622A which discloses a method for achieving the illusion of a stereoscopic image by using two alternately illuminated light sources.

Additional image enhancement techniques are shown in U.S. Pat. Nos. 5,728,044 and 5,575,754 which disclose endoscopes that make use of an additional sensor to provide location measurements of image points and in U.S. Pat. No. 6,009,189 which provides for image acquisition from different directions using one or more cameras.

The major limiting factor associated with current endoscopes is the inability to adequately light the object for imaging. For any type of photographic imaging, there must exist adequate illumination. Thus, the typical endoscope generally includes an illumination source which disperses light throughout the field of interest. However, many interior spaces of the body are problematic to illuminate sufficiently for imaging. For example, surgery on certain internal parts of the body require that relatively large areas be illuminated simultaneously because the surgery involves numerous objects at different distances from one another. Therefore, in many surgical fields of view, the distances of objects of interest from the illumination source can easily range between 2 and 20 cm, resulting in a distance ratio of 1:10. The corresponding brightness ratio may then be 1:100, causing blinding and making the distant objects all but invisible. Accordingly, the issue of regulation of illumination levels has been approached in a number of prior art sources, including U.S. Pat. No. 4,967,269 and Japan Patent Nos. 61018915A, 4236934A, 8114755A and 8024219A.

Another reason for difficulty in endoscopic illumination is that the field of view desired is often located within an opaque medium, such as blood. This problem has not been successfully solved and therefore effective endoscopic surgery is not widely available for many heart and blood vessel diseases, which are among the main causes for morbidity and mortality in Western society today.

The pathology that is the base of most acute coronary syndromes and sudden cardiac deaths is atherosclerosis. In this process, atherosclerotic plaque, which is an active collection of immune cells and smooth muscle cells along with deposits of fats, cholesterol, cellular waste products, calcium and other substances, is accumulated in the inner lining of an artery. Such adhered and stable plaques, which cause the more significant narrowing of the arterial wall, are considered the major factor in the development of angina pectoris. However, studies from recent years have shown that angina, myocardial infarctions and sudden cardiac related deaths are often caused by unstable plaques, also known as vulnerable plaques. These unstable plaques consist mainly of unadhered particles of the same materials as the stable plaque. If released into the bloodstream, these particles may cause small occlusions in the coronary arteries and may also cause occlusions in small blood vessels of other organs, such as the brain, kidney, or lungs. Such unstable plaque is usually smaller and therefore more difficult to detect with currently used angiographic methods, particularly the minimally invasive procedures.

Angiography is a commonly used method for imaging within the heart and coronary blood vessels. Angiography involves using an X-ray camera positioned outside the body as the imaging device, and introducing a contrast substance via a catheter into the heart and associated blood vessels to enable them to be viewed by the X-ray camera. Angiography gives a two-dimensional monochromatic view of the heart and blood vessels as viewed from the outside. This method detects occlusions by identifying places where blood flow is restricted and may further be used to direct a stent delivery system to the occlusion location, including insertion of any percutaneous transluminal coronary angioplasty device or stent. However, angiography does not give a direct view of the occlusion site nor of the plaque itself. Therefore, minimally invasive surgery performed using angiography as its visual guide carries with it a major risk of merely rupturing or disrupting the fibrous cap covering the stable plaque and consequently releasing newly unstable plaque particles into the blood stream.

Another approach to imaging in blood is to utilize infrared (IR) light to enable visibility through the suspended particles and cells in the blood. A patent that discloses a method for using deep-IR light for imaging through blood is U.S. Pat. No. 6,178,346. However, the use of deep-IR wavelengths to achieve visibility in a blood medium as described therein requires very high-energy illumination, which has risks and disadvantages when used inside the body. The use of near-IR radiation substantially diminishes risks but results in a lower resolution image. U.S. Pat. No. 4,953,539 discusses the use of endoscopic imaging using IR illumination from outside the body. It is a well-known property of human tissue to have different absorption, scattering, and attenuation coefficients of IR radiation. Thus, different types of tissues may be clearly distinguished using IR imaging techniques. However, such external illumination does not produce high quality images and has not been used to date for intra-vascular imaging. A discussion of the use of IR illumination for medical imaging is found in "A Review of the Optical Properties of Biological Tissues" Cheong, Prahl and Welch, IEEE J. of Quantum Electronics, Vol. 26, 12 Dec. 1990.

Other methods currently used to provide intra-vascular imaging include integrating endoscopes with other forms of imaging such as intra-luminal ultrasound as disclosed in U.S. Pat. No. 4,869,256 and Optical Coherence Tomography, which provides a three dimensional image by performing optical measurements. Related patents include; U.S. Pat. Nos. 6,129,672; 6,099,475; 6,039,693; 6,134,003 and 6,010,449. The imaging methods disclosed also do not provide high quality, high resolution images.

Other methods for enabling visibility within opaque fluids with intra-vascular applications are disclosed in U.S. Pat. Nos. 4,576,146; 4,827,907; 4,934,339; 4,998,972; 5,010,875 and 6,178,346. None of the methods disclosed provide sufficiently high quality images. For a comprehensive discussion of light transference through blood and different mediums, see "Optical Properties of Circulating Human Blood in Wavelength Range 400-2500 nm" Andre Roggan, Journal of Biomedical Optics, January 1999.

The optical parameters and characteristics of blood that effect visibility therethrough are primarily the absorption and the scattering of light. Normal human blood consists of 55% liquid and 45% cells. The liquid fraction is known as the plasma, and is composed of 90% water and 10% proteins. The cellular fraction is usually composed of 99% erythrocytes (red blood cells) and 1% leukocytes and thrombocytes. The component of blood that has the most significant optical effect is that of the red blood cells (RBC), primarily because of their high volume, which averages $5 \times 10^6$ RBC per microliter. Because of this very high concentration, virtually all light emitted into blood is either absorbed or scattered, making photographic imaging difficult. It has been found that the absorption and scattering coefficients of light emitted into blood vary according to wavelength in such a way that either the absorption is very high or the scattering is very high, making it virtually impossible to acquire clear and useful images using light in any wavelength from 400 nm to 2500 nm.

Of the two effects, the major impediment to acquiring images through flowing blood arises from the reflectance and consequent scattering of light by the red blood cells. Such scattering makes it impossible for a light receptor to distinguish the light reflected from structures within the blood vessel (the "signal") from the light reflected from the flowing red blood cells "noise"). No photographic imaging method to date has successfully increased the signal/noise ratio sufficiently to overcome this impediment.

Accordingly, the need for better visibility during vascular procedures is universally acknowledged. There is thus a widely recognized need for, and it would be highly advantageous to have, an intravascular imaging apparatus that provides high quality images.

SUMMARY OF THE INVENTION

It is an object of the present invention to provide a minimally invasive imaging apparatus, system and method which allow the acquisition of high resolution images through opaque media, particularly blood.

It is a further object of the present invention to provide an imaging apparatus, system and method which will provide a direct and clear view of an object within an intravascular environment.

It is a yet further object of the present invention to provide an imaging apparatus, system and method which will provide an image of a field of view within an intravascular environment sufficient to allow diagnostic and therapeutic procedures to be carried out therein.

It is a still further object of the present invention to provide an imaging apparatus, system and method which will provide an image of a field of view within an intravascular environment sufficient to allow diagnostic and therapeutic procedures to be carried out without inadvertent damage, such as the disruption of plaques within the intravascular environment.

According to one aspect of the present invention there is provided an apparatus for providing an image of a target region located within an intravascular environment, the apparatus comprising (a) a camera having at least one light sensing region; (b) at least one light source for emitting polarized light to impinge upon the target region; and (c) at least one polarization filter for filtering out non-polarized light, the filter being disposed on the light path such that light reflected from the target region passes through the filter before being detected by the light sensing region, thereby reducing the amount of non-polarized light detected by the camera.

According to another aspect of the present invention there is provided an apparatus for providing an image of a target region located within an intravascular environment, the apparatus comprising (a) a camera having at least one light sensing region for detecting light, and (b) at least one light source for emitting light to impinge upon the target region, the light reflected from the target region being detected at said light sensing region; the apparatus associated with image processing functionality for reconstruction of at least one image from light detected by the light sensing region, the reconstruction being based upon expected light reflection behavior for light emitted within a continuous tubular structure in order to recognize and exclude reflected light that is not expected according to the behavior.

According to another aspect of the present invention there is provided an apparatus for providing an image of a target region located within an intravascular environment, the apparatus comprising (a) a camera having at least one light sensing region for detecting light, and (b) at least one light source for emitting light to impinge upon the target region, the light reflected from the target region being detected at said light sensing region; the apparatus associated with image processing functionality for reconstruction of at least one image from light detected by the light sensing region, the reconstruction being based upon expected light reflection behavior within a two directional pulse related intravascular fluid movement in order to recognize and exclude reflected light that is expected according to the expected behavior.

According to another aspect of the present invention there is provided an apparatus for providing an image of a target region located within an intravascular environment, the apparatus comprising (a) a camera having at least one light sensing region for detecting light, and (b) at least one light source for emitting light to impinge upon the target region, the light reflected from the target region being detected at said light sensing region; the apparatus associated with image processing functionality for reconstruction of at least one image from light detected by the light sensing region, the reconstruction being based upon expected light reflection behavior within a pulse related radially expanding and contracting vascular vessel in order to recognize and exclude reflected light that is not expected according to the expected behavior.

According to another aspect of the present invention there is provided an apparatus for providing an image of a target region located within an intravascular environment, the apparatus comprising (a) a camera having at least one light sensing region, and (b) at least one light source for emitting light to impinge upon the target region, the light source being controllable to emit the light to impinge upon a predetermined field including the target region and substantially excluding surroundings of the target region, thereby to reduce an amount of reflected light generated by the surroundings from reaching the light sensing region.

According to features in the described preferred embodiments, the intravascular environment is within a vein or an artery and the target region includes the interior wall of the vein or artery and matter in contact with the interior wall.

According to further features in the described preferred embodiments, the polarization filter is attached to the light sensing region.

According to still further features in the described preferred embodiments, the polarization filter is for filtering out light not repolarized by reflection from the target region.

According to still further features in the described preferred embodiments, the polarization filter comprises a plurality of separately orientated filtering regions.

According to still further features in the described preferred embodiments, the light sensing region comprises a plurality of pixels and each of the plurality of separately orientated filtering regions is associated with one of the pixels.

According to still further features in the described preferred embodiments, a first portion of the plurality of filtering regions is designed and configured at a first predetermined polarization orientation and a second portion of the plurality of filtering regions is designed and configured at a second predetermined polarization orientation perpendicular to the first polarization orientation.

According to still further features in the described preferred embodiments, the number of filtering regions within the first portion is substantially equal to the number of filtering regions within the second portion.

According to still further features in the described preferred embodiments, the filtering regions of the first portion are interspersed with the filtering regions of the second portion.

According to still further features in the described preferred embodiments, the at least one light sensing region comprises two light sensing regions; the at least one light source comprises two light sources, the two light sources being for respectively emitting light for detection by the two light sensing regions; and the at least one polarization filter comprises two polarization filters, the two polarization filters being positioned such that they respectively filter the light prior to detection by the two light sensing regions.

According to still further features in the described preferred embodiments, each of the two light sources is for emitting polarized light with a different polarization angle.

According to still further features in the described preferred embodiments, the polarization angles are within a plane parallel to a longitudinal axis of the intravascular environment.

According to still further features in the described preferred embodiments, the different polarization angles are perpendicular to one other.

According to still further features in the described preferred embodiments, the at least one light sensing region comprises a plurality of light sensing regions; the at least one light source comprises a plurality of light sources, the plurality of light sources being for emitting light for detection by the plurality of light sensing regions; the at least one polarization filter comprises a plurality of polarization filters, the polarization filters being positioned such that they respectively filter the light prior to detection by the light sensing regions.

According to still further features in the described preferred embodiments, a first portion of the plurality of light sources is for emitting polarized light with a first specific polarization angle and a second portion of the plurality of light sources is for emitting light with a second different specific polarization angle.

According to still further features in the described preferred embodiments, the polarization angles are within a plane parallel to a longitudinal axis of the intravascular environment.

According to still further features in the described preferred embodiments, the first specific polarization angle is perpendicular to the second specific polarization angle.

According to still further features in the described preferred embodiments, the light source is controllable to emit the light in time sequential flashes.

According to still further features in the described preferred embodiments, the light source is controllable to emit the light in a range of intensities.

According to still further features in the described preferred embodiments, the light source is controllable to emit the light in a range of wavelengths.

According to still further features in the described preferred embodiments, the light source is a point source.

According to still further features in the described preferred embodiments, the light source is controllable to emit the light for a predefined period.

According to still further features in the described preferred embodiments, the apparatus further comprises a shutter located in association with the light sensing region to define a sensing period and operatively associated with the light source to co-ordinate the sensing period with the predefined emitting period.

According to still further features in the described preferred embodiments, the apparatus further comprises a guide member for inserting the apparatus into the intravascular environment, the apparatus being positioned upon a distal end of the guide member.

According to still further features in the described preferred embodiments, the guide member is a catheter having at least one open tubular channel oriented longitudinally therein.

According to still further features in the described preferred embodiments, the apparatus further comprises a light meter for measuring the optical properties within the intravascular environment in proximity to the camera.

According to still further features in the described preferred embodiments, the apparatus further comprises at least one device for altering optical properties within the intravascular environment in proximity to the camera.

According to still further features in the described preferred embodiments, the apparatus further comprises a control unit for operating the at least one device in accordance with a predetermined procedure for balancing between visibility and non-interference with blood supply.

According to still further features in the described preferred embodiments, the at least one device is a fluid injector for injecting a fluid into the intravascular environment in order to alter the optical properties of blood within the optical path of the emitted light, such that the blood provides less interference with the passage therethrough of the light.

According to still further features in the described preferred embodiments, the fluid is capable of carrying oxygen.

According to still further features in the described preferred embodiments, the at least one device is a fluid displacer for displacing blood from the optical path of the emitted light.

According to still further features in the described preferred embodiments, the apparatus further comprises a processor.

According to still further features in the described preferred embodiments, the processor is for receiving data related to the optical environment within the intravascular environment and for using the data to determine at least one optical requirement needed for imaging within the intravascular environment.

According to still further features in the described preferred embodiments, the processor is for using the data to determine at least one operational command for actions needed in order to meet the at least one optical requirement.

According to still further features in the described preferred embodiments, the commands relate to the optical performance of apparatus.

According to still further features in the described preferred embodiments, the commands relate to altering optical properties within intravascular environment.

According to still further features in the described preferred embodiments, the processor is for receiving data associated with light detected by the light sensing region, and for reconstructing at least one image from the received data.

According to still further features in the described preferred embodiments, the apparatus further comprises a graphic user interface including at least one user control for operating the apparatus and a display for displaying at least one image of the target region.

According to still further features in the described preferred embodiments, the apparatus further comprises a communication unit for conveying data to and from the imaging apparatus.

According to still further features in the described preferred embodiments, the apparatus forms part of a diagnostic or therapeutic system, the system further comprising at least one control device for controlling the apparatus, at least one communication unit and at least one display device.

According to another aspect of the present invention there is provided a system for providing an image of a target region located within an intravascular environment, the system comprising (a) an imaging apparatus including a camera having at least one light sensing region for detecting light, at least one light source for emitting polarized light to impinge upon the target region, and at least one polarization filter for polarization filtering the light, the filter being disposed in the light path such that light reflected from the target region passes through the filter before being detected by the light sensing region; and (b) one or more selected from the group consisting of (i) image processing functionality for reconstruction of at least one image from light detected by the light sensing region, the reconstruction being based upon expected light reflection behavior for light emitted within a continuous tubular structure in order to recognize and exclude reflected light that is not expected according to the behavior, (ii) image processing functionality for reconstruction of at least one image from light detected by the light sensing region, the reconstruction being based upon expected light reflection behavior within a two directional pulse related intravascular fluid movement in order to recognize and exclude reflected light that is expected according to the expected behavior, (iii) image processing functionality for reconstruction of at least one image from light detected by said light sensing region, the reconstruction being based upon expected light reflection behavior for light emitted within a pulse related radially expanding and contracting vascular vessel in order to recognize and exclude light that is not expected according to the expected behavior; (iv) a graphic user interface including at least one control for entering at least one user command and a visual display for displaying at least one image of the target region; (v) a processor for receiving data related to the optical environment within the intravascular environment, for using the data to determine at least one optical requirement for imaging within the intravascular environment, for determining at least one operational command to carry out at least one action needed in order to meet at least one optical requirement, for receiving data associated with light detected by the light sensing region, and for carrying out the image processing functionality; (vi) a communication unit for conveying optical data to the processor, for conveying at least one operational command to the imaging apparatus, for conveying data from the imaging apparatus to the processor, and for conveying data representing at least one reconstructed image to a viewable location; (vii) a guide member for inserting the imaging apparatus into the intravascular environment, the imaging apparatus being positioned upon the distal end of the guide member; (viii) a light meter for measuring the optical properties within the intravascular environment in proximity to the camera; and (ix) at least one device for altering optical properties within the intravascular environment in proximity to the camera.

According to another aspect of the present invention there is provided a system for providing an image of a target region located within an intravascular environment, the system comprising (a) an imaging apparatus including a camera having at least one light sensing region for detecting light, at least one light source for emitting light to impinge upon the target region, the light reflected from the target region being detected by the light sensing region; (b) image processing functionality for reconstruction of at least one image from light detected by the light sensing region, the reconstruction being based upon expected light reflection behavior for light emitted within a continuous tubular structure in order to recognize and exclude reflected light that is not expected according to the behavior; and (c) one or more selected from the group consisting of (i) image processing functionality for reconstruction of at least one image from light detected by the light sensing region, the reconstruction being based upon expected light reflection behavior within a two directional pulse related intravascular fluid movement in order to recognize and exclude reflected light that is expected according to the expected behavior; (ii) image processing functionality for reconstruction of at least one image from light detected by said light sensing region, the reconstruction being based upon expected light reflection behavior for light emitted within a pulse related radially expanding and contracting vascular vessel in order to recognize and exclude light that is not expected according to the expected behavior; (iii) a graphic user interface including at least one control for entering at least one user command and a visual display for displaying at least one image of the target region; (iv) a processor for receiving data related to the optical environment within the intravascular environment, for using the data to determine at least one optical requirement for imaging within the intravascular environment, for determining at least one operational command to carry out at least one action needed in order to meet at least one optical requirement, for receiving data associated with light detected by the light sensing region, and for carrying out the image processing functionality (v) a communication unit for conveying optical data to the processor, for conveying at least one operational command to the imaging apparatus, for conveying data from the imaging apparatus to the processor, and for conveying data representing at least one reconstructed image to a viewable location; (vi) a guide member for inserting the imaging apparatus into the intravascular environment, the imaging apparatus being positioned upon the distal end of the guide member; (vii) a light meter for measuring the optical properties within the intravascular environment in proximity to the camera; and (viii) at least one device for altering optical properties within the intravascular environment in proximity to the camera.

According to another aspect of the present invention there is provided a system for providing an image of a target region located within an intravascular environment, the system comprising (a) an imaging apparatus including a camera having at least one light sensing region for detecting light, at least one light source for emitting light to impinge upon the target region, the light reflected from the target region being detected by the light sensing region; (b) image processing functionality for reconstruction of at least one image from light detected by the light sensing region, the reconstruction being based upon expected light reflection behavior within a two directional pulse related intravascular fluid movement in order to recognize and exclude reflected light that is expected according to the expected behavior; and (c) one or more selected from the group consisting of (i) image processing functionality for reconstruction of at least one image from light detected by said light sensing region, the reconstruction being based upon expected light reflection behavior for light emitted within a pulse related radially expanding and contracting vascular vessel in order to recognize and exclude light that is not expected according to the expected behavior; (ii) a graphic user interface including at least one control for entering at least one user command and a visual display for displaying at least one image of the target region; (iii) a processor for receiving data related to the optical environment within the intravascular environment, for using the data to determine at least one optical requirement for imaging within the intravascular environment, for determining at least one operational command to carry out at least one action needed in order to meet at least one optical requirement, for receiving data associated with light detected by the light sensing region, and for carrying out the image processing functionality; (iv) a communication unit for conveying optical data to the processor, for conveying at least one operational command to the imaging apparatus, for conveying data from the imaging apparatus to the processor, and for conveying data representing at least one reconstructed image to a viewable location; (v) a guide member for inserting the imaging apparatus into the intravascular environment, the imaging apparatus being positioned upon the distal end of the guide member, (vi) a light meter for measuring the optical properties within the intravascular environment in proximity to the camera; and (vii) at least one device for altering optical properties within the intravascular environment in proximity to the camera.

According to another aspect of the present invention there is provided a system for providing an image of a target region located within an intravascular environment, the system comprising (a) an imaging apparatus including a camera having at least one light sensing region for detecting light, at least one light source for emitting light to impinge upon the target region, the light reflected from the target region being detected by the light sensing region; (b) image processing functionality for reconstruction of at least one image from light detected by said light sensing region, the reconstruction being based upon expected light reflection behavior for light emitted within a pulse related radially expanding and contracting vascular vessel in order to recognize and exclude light that is not expected according to the expected behavior; and (c) one or more selected from the group consisting of (i) a graphic user interface including at least one control for entering at least one user command and a visual display for displaying at least one image of the target region; (ii) a processor for receiving data related to the optical environment within the intravascular environment, for using the data to determine at least one optical requirement for imaging within the intravascular environment, for determining at least one operational command to carry out at least one action needed in order to meet at least one optical requirement, for receiving data associated with light detected by the light sensing region, and for carrying out the image processing functionality; (iii) a communication unit for conveying optical data to the processor, for conveying at least one operational command to the imaging apparatus, for conveying data from the imaging apparatus to the processor, and for conveying data representing at least one reconstructed image to a viewable location; (iv) a guide member for inserting the imaging apparatus into the intravascular environment, the imaging apparatus being positioned upon the distal end of the guide member, (v) a light meter for measuring the optical properties within the intravascular environment in proximity to the camera; and (vi) at least one device for altering optical properties within the intravascular environment in proximity to the camera.

According to another aspect of the present invention there is provided a system for providing an image of a target region located within an intravascular environment, the system comprising (a) an imaging apparatus including a camera having at least one light sensing region for detecting light, and at least one light source for emitting light to impinge upon a predetermined field including the target region and substantially excluding surroundings of the target region, thereby to reduce surrounding-induced reflected light from being detected by the light sensing region, the light reflected from the target region being detected by the light sensing region; and (b) one or more selected from the group consisting of (i) a graphic user interface including at least one control for entering at least one user command and a visual display for displaying at least one image of the target region; (ii) a processor for receiving data related to the optical environment within the intravascular environment, for using the data to determine at least one optical requirement for imaging within the intravascular environment, for determining at least one operational command to carry out at least one action needed in order to meet at least one optical requirement, for receiving data associated with light detected by the light sensing region, and for carrying out the image processing functionality; (iii) a communication unit for conveying optical data to the processor, for conveying at least one operational command to the imaging apparatus, for conveying data from the imaging apparatus to the processor, and for conveying data representing at least one reconstructed image to a viewable location; (iv) a guide member for inserting the imaging apparatus into the intravascular environment, the imaging apparatus being positioned upon the distal end of the guide member, (v) a light meter for measuring the optical properties within the intravascular environment in proximity to the camera; and (vi) at least one device for altering optical properties within the intravascular environment in proximity to the camera.

According to yet another aspect of the present invention there is provided a method for providing an image of a target region located within an intravascular environment, the method comprising (a) inserting an imaging apparatus into the intravascular environment in proximity to the target region; (b) emitting polarized light from a light source to impinge upon the target region; (c) polarization filtering the light after at least some of the light is reflected from the target region; (d) detecting the polarization filtered light; and (e) reconstructing at least one image based upon the detected polarization filtered light.

According to still another aspect of the present invention there is provided a method for providing an image of a target region located within an intravascular environment, the method comprising (a) inserting an imaging apparatus into the intravascular environment in proximity to the target region; (b) emitting light from a light source to impinge upon the target region; (c) detecting the light; and (d) reconstructing at least one image from the detected light based upon expected light reflection behavior for light emitted within a continuous tubular structure in order to recognize and exclude reflected light that is not expected according to behavior.

According to an additional aspect of the present invention there is provided a method for providing an image of a target region located within an intravascular environment, the method comprising (a) inserting an imaging apparatus into the intravascular environment in proximity to the target region; (b) emitting light from a light source to impinge upon the target region; (c) detecting the light; and (d) reconstructing at least one image from the detected light based upon expected light reflection behavior within a two directional pulse related intravascular fluid movement in order to recognize and exclude reflected light that is expected according to the expected behavior.

According to a further additional aspect of the present invention there is provided a method for providing an image of a target region located within an intravascular environment, the method comprising (a) inserting an imaging apparatus into the intravascular environment in proximity to the target region; (b) emitting light from a light source to impinge upon the target region; (c) detecting the light; and (d) reconstructing at least one image from the detected light based upon expected light reflection behavior for light emitted within a pulse related radially expanding and contracting vascular vessel in order to recognize and exclude reflected light that is not expected according to the expected behavior.

According to yet another additional aspect of the present invention there is provided a method for providing an image of a target region located within an intravascular environment, the method comprising (a) inserting an imaging apparatus into the intravascular environment in proximity to the target region; (b) emitting light to impinge upon a predetermined field which includes the target region and substantially excludes surroundings of the target region, thereby to reduce surrounding-induced reflected light from being detected; and (c) detecting the light; and (d) reconstructing at least one image from the detected light based upon the reduced surrounding-induced reflected light.

According to features in the described preferred embodiments, the method further comprises conveying data representing at least one reconstructed image of the target region to a viewable location.

According to further features in the described preferred embodiments, the method further comprises providing for graphical user interfacing including providing at least one graphical control for entering at least one user command and displaying at least one reconstructed image.

The present invention successfully addresses the shortcomings of the presently known configurations by providing an imaging apparatus, system and method which can provide a high resolution image of a field of view within an intravascular environment sufficient to allow diagnostic and therapeutic procedures to be carried out therein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a schematic illustration of an apparatus for intravascular imaging in accordance with a preferred embodiment of the present invention;

FIG. 2 is a representational illustration of a pixilated light sensing region of the apparatus of FIG. 1;

FIG. 3 is a representational illustration of a filter of the apparatus of FIG. 1;

FIG. 5 is a flow diagram illustrating an inflation control algorithm for use by the device of FIG. 7a;

FIG. 11 is a schematic illustration of a system for providing an image in accordance with a preferred embodiment of the present invention;

FIG. 12 is a flow diagram illustrating a preferred embodiment of a method for providing an image in accordance with the present invention;

FIG. 13 is a flow diagram illustrating a further preferred embodiment of a method for providing an image in accordance with the present invention.

DESCRIPTION OF THE PREFERRED EMBODIMENTS

Figure 4:
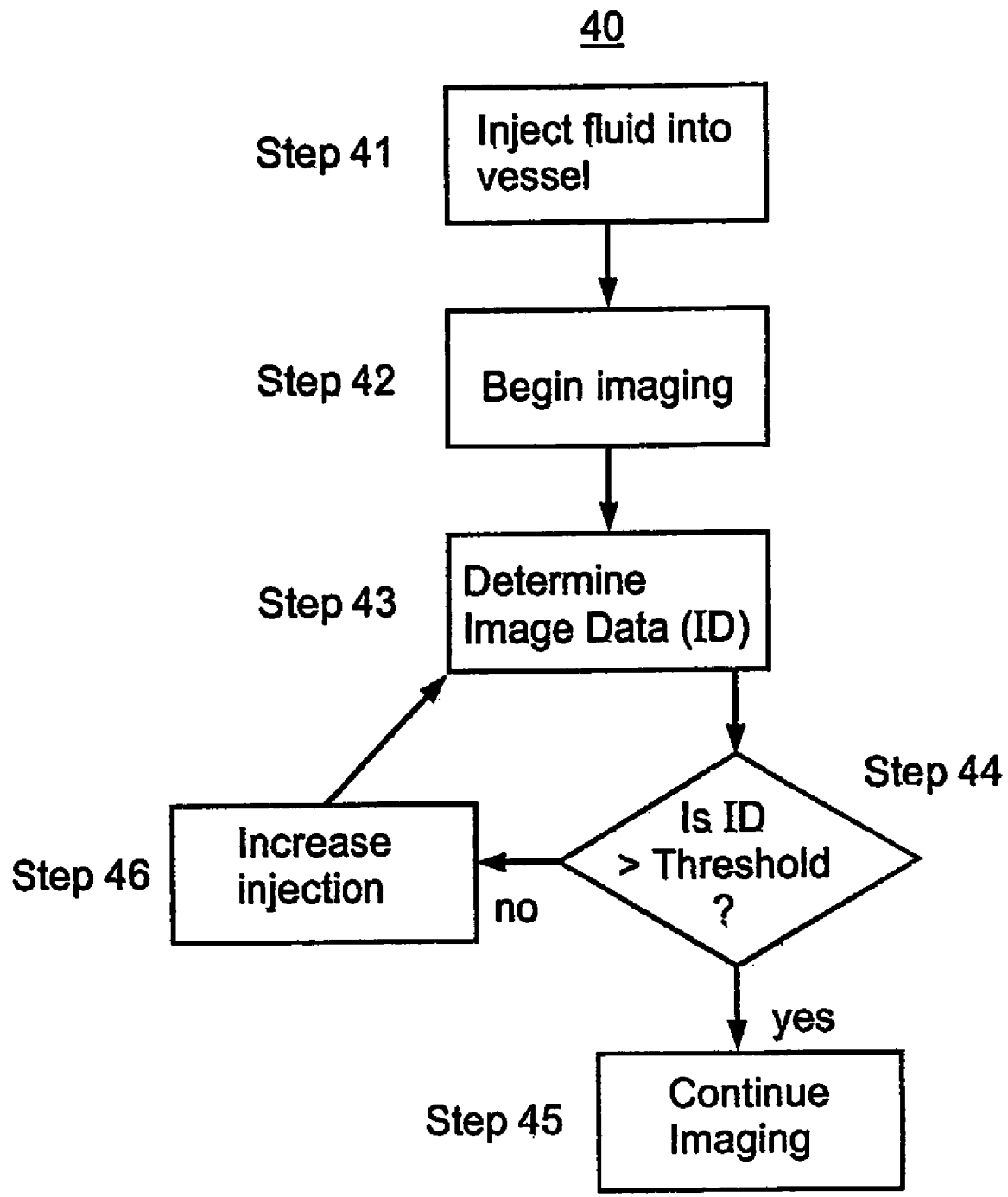
FIG. 4 is a flow diagram illustrating an injection control algorithm for use by the apparatus of FIG. 1.

The present invention is of an apparatus, system and method for providing an image of a target region within an intravascular environment. The intravascular environment is preferably a vein or an artery and the target region is preferably the interior vessel wall, including any material or growth that may be attached to or adjacent to the vessel wall. Specifically, the present invention is for providing an image from within an intravascular environment that contains a relatively opaque medium, such as blood. The present invention provides an enhanced photographic image of the target region that is superior in quality and resolution to images provided by current intravascular imaging processes.

The present invention is subject to implementation in a number of different embodiments, each of which has an image enhancing effect which will be described in detail hereinafter. Each of the embodiments may be implemented alone or in combination with any one or more of the other embodiments. A preferred embodiment of the present invention is a combination of embodiments, preferably most or all of the embodiments, implemented together in order to gain the benefit of the image enhancing effects of each of the embodiments simultaneously.

The present invention may be used for all types of photographic imaging, including but not limited to still photography, stereoscopic or three dimensional still photography, video and streaming video. Moreover, it is understood that the present invention may be used with a wide variation in wavelengths of light, resulting in both color and monochromatic images as well as visible images and invisible images that are digitally or graphically represented.

As used herein, the term "image" refers to any pictorial, graphic and/or alphanumeric information provided based upon light detected by the apparatus, system and method herein described; the term "signal" refers to light reflected from the object of interest within the target region; and the term "noise" refers to light reflected from objects within the target region other than the object of interest or to any ambient light not reflected from the object of interest.

Before explaining each of the embodiments of the invention in detail, it is to be understood that the invention is not limited in its application to the details of construction and the arrangement of the components set forth in the following descriptions or illustrated in the drawings. The invention is capable of other embodiments and variations of described embodiments. Also, it is expected that during the life of this patent many relevant photographic apparatuses, systems, methods and techniques will be developed and the scope of the term imaging is intended to include all such new technologies a priori. Moreover, it is to be understood that the phraseology and terminology employed herein is for the purpose of description and should not be regarded as limiting.

The principles and operation of an apparatus, system and method according to the present invention may be better understood with reference to the drawings and accompanying descriptions.

Referring now to the drawings, FIG. 1 is a schematic illustration of an apparatus for intravascular imaging in accordance with an embodiment of the present invention, referred to hereinafter as endoscope 10. The embodiment shown in FIG. 1 involves the use of polarization properties of light in order to identify signal components and reject noise components. FIG. 1 is also pertinent to other hereinafter described embodiments which may use polarized or unpolarized light and which rely upon other optical or image reconstruction features to identify signal components and reject noise components and thereby to enhance imaging.

Endoscope 10 comprises a camera 12 having a light sensing region 14 for detecting light, which may comprise one, two or a plurality of pixels. Sensing region 14 may further consist of two sensing regions or a plurality of sensing regions, each of which in themselves may comprise one, two or a plurality of pixels. FIG. 2 is a representational illustration of a pixilated light sensing region showing how the pixels of a representative sensing region 14 may be arrayed. It is understood that any arrangement of pixels may be employed according to the imaging requirements.

Camera 12 may be any of many known endoscopic cameras, and may have CMOS or CCD based sensing regions 14. Such light sensors are well known in the art and are commonly in use. Accordingly, sensing region 14, irrespective of its configuration into one sensing region or two or more sensing regions, may be arranged in any appropriate shape and size for endoscopic use. A preferred but not essential arrangement is for sensing region 14 to be rectangular in shape, such as a 128×256 pixel array, with the desired number of sensing regions positioned successively longitudinally along endoscope 10. It is understood that sensing region 14 is designed to detect light reflected from the interior wall of the vascular vessel and therefore sensing region 14 is preferably oriented substantially parallel to the longitudinal interior wall, and at least not perpendicular thereto.

Endoscope 10 further comprises at least one light source, hereinafter referred to as light source 16, for emitting light to impinge upon a target region within the intravascular environment. Light source 16 may preferably be an LED or other appropriate source and is positioned and oriented such that at least a portion of the light that it emits is reflected by the target region to be detected by sensing region 14. Light source 16 may be a point source or a more diffused source as needed according to the requirements of the embodiment described.

Light source 16 is preferably controlled to emit light to impinge upon a restricted or limited field. In accordance with a further embodiment of the present invention, light source 16 emits light to impinge upon a predetermined field which includes the part or region of the vascular wall currently being scanned and substantially excludes the surroundings of the target region. Accordingly, endoscope 10 includes the capability to move and/or to focus light source 16 in order to illuminate a target region of interest and to minimize the illumination of the surroundings of the target region. The purpose of such restricted illumination is to reduce the amount of surrounding-induced reflected light detected by sensing region 14. This further embodiment will be fully described hereinafter.

Light source 16 may emit any visible or invisible light as required. The selection of light to be used is significant with respect to imaging within an intravascular environment. There are three properties of light that effect its ability to pass through a medium: scattering, absorption, and attenuation. Scattering is significant for light in the visible, IR and near-IR (wavelengths shorter than 1 μm) spectrum when passing through blood. Absorption and attenuation, on the other hand, are minimal with near-IR light. Therefore, near-IR light may be preferable to visible light for effective illumination through such a medium as blood. The type of light used is not a material element of the present invention.

Light source 16 may comprise two separate light sources or a plurality of separate light sources when endoscope 10 is respectively configured with two sensing regions 14 or a plurality of sensing regions 14. Each light source emits light to be detected by one of the sensing regions 14. According to such multiple light source configurations, substantially half of the light sources may emit light at different intensities or with different energy emissions as the other half of the light sources in order to provide different spectral images. For example, a half of the light sources 16 may emit visible light for producing a visible spectrum image and a second half of the light sources 16 may emit invisible light, either IR or UV, for producing a corresponding spectral response image. Moreover, each half may be separately controllable to produce a desired ratio of visible and invisible images. Further, each half of the light sources may be separately controlled in order to emit at different times, or to emit light in time sequential flashes or for a predefined period, in which case endoscope 10 will further comprise a shutter 18 located in association with sensing region 16 which defines a sensing period and will be operatively associated with light source 16 to co-ordinate the sensing period with the predefined emitting period.

Each half of the light sources may be oriented to emit light toward different fields or in different directions, according to specific imaging, such as 3D or variable lighting to illuminate a wide field.

According to one embodiment, light source 16 is preferably for emitting polarized light According to further embodiments, light source 16 is also for emitting non-polarized light.

According to the embodiment in which polarized light is emitted, light source 16 may comprise two light sources which may be configured such that each light source emits light with a specific and different polarization angle. In such a configuration, the different polarization angles are preferably perpendicular to one another and are both within a plane parallel to the longitudinal axis of the vascular vessel. Further according to such an embodiment, light source 16 may comprise a plurality of light sources which may be configured such that a first portion of light sources emits light with a different polarization angle than the light emitted by a second portion of light sources. In such a configuration, the different polarization angles are preferably perpendicular to one another and are all within a plane parallel to the longitudinal axis of the vascular vessel.

According to the embodiment in which polarized light is emitted, endoscope 10 further comprises at least one polarization filter, hereinafter referred to as filter 20, for polarization filtering of light arriving at the sensor. More specifically, filter 20 is for filtering out light not repolarized by reflection from the vascular wall as will be described in greater detail below. According to embodiments in which non-polarized light is emitted, filter 20 may be any other type of filter, such as a wavelength filter, for any image enhancement purpose. Filter 20 is disposed on the light path such that light reflected from the target region passes through it before being detected by sensing region 14. Filter 20 may preferably be attached to or positioned adjacent to sensing region 14.

In configurations of endoscope 10 in which sensing region 14 comprises two or a plurality of sensing regions 14, Filter 20 will respectively comprise two or a plurality of filters 20, each of which is associated with one of the sensing regions and is positioned such that it filters light prior to detection by its respectively associated sensing region 14.

Further, filter 20 may preferably comprise a plurality of separately oriented filtering regions, each of which is associated with one pixel of a sensing region 14. According to such multiple filtering region configurations, substantially half of the filtering regions will be designed and configured at a first predetermined polarization orientation and the other substantial half of the filtering regions will be designed and configured at a second predetermined polarization orientation which is perpendicular to the first polarization orientation. According to the preferred embodiment, the filtering regions configured at the first predetermined polarization orientation are interspersed with filtering regions configured at the second predetermined polarization orientation. FIG. 3 is a representational illustration of filter 20 with separate filtering regions interspersed. It is noted that the interspersion of the filtering regions coincides with the configuration of the pixels of sensing region 14 displayed in FIG. 2, such that each polarization orientation coincides with a corresponding polarization angle of the pixel of light which it is designed to filter.

Endoscope 10 may also employ any other optical assembly, not shown, as needed for imaging according to the described embodiments, including such optical elements as lenses, mirrors, irises, prisms, image distorters, image separators, shutters and the like and also preferably comprises an optical processor, not shown, for converting detected light into electrical signals which are digitized and transmitted to a processor for image reconstruction and viewing.

Endoscope 10 further comprises a guide member for inserting endoscope 10 into a vascular vessel. The guide member may be a wire or a catheter as is well known in the art. Endoscope 10 may also employ one or more open tubular channels oriented longitudinally for the purpose of altering optical properties within the intravascular vessel, as will be described more fully hereinafter, or for carrying out therapeutic treatment therethrough. A channel for a guide wire is preferable, which may be provided as a dedicated channel for the guide wire only or may be combined with a working channel.

Endoscope 10 further comprises a communication link 28 for conveying data to and from endoscope 10 such that optical information may be conveyed, commands received and data transmitted to a processor for image reconstruction. Link 28 may be a wired link, in which case a wire will run from endoscope 10 to the processor, or a wireless link, such as IR, Radio Frequency or other wireless communication methods and technologies that may be appropriate.

Endoscope 10 preferably comprises a processor, not shown, for receiving information related to the optical environment within the intravascular vessel and for using that information to determine any optical requirements needed for imaging therein. The processor also uses that information to determine any operational commands for actions needed in order to meet the optical requirements. Such commands typically relate to the optical performance of endoscope 10, much as a standard camera is adjusted to take photographs under any given light conditions. The commands may also relate to altering optical properties within the intravascular vessel, as will be described more fully hereinafter with respect to further embodiments of the invention. The processor also receives data associated with light detected by sensing region 14 and reconstructs images from the received data. Such images are reconstructed by running predefined image reconstruction algorithms for defining the parameter values by which detected light is judged, in accordance with further embodiments of the invention, which will be more fully described hereinafter.

Endoscope 10 further preferably comprises a graphic user interface, not shown, which includes at least one user control for operating endoscope 10 by providing commands related to the optical performance, and a display for displaying reconstructed images from within the intravascular vessel.

Like most cameras, endoscope 10 further comprises a light meter 30 for measuring the optical properties within the vascular vessel in proximity to camera 12, specifically, the area in which it will capture images. Many different types of light meter are possible for endoscopic use and the specific type is not a material element of the invention.

In addition, endoscope 10 further comprises a power supply, also not shown, which may be provided from an external source or may be a battery for portable use. This too is not a material element of the invention.

Because the imaging function of endoscope 10 takes place within an opaque medium, it is a preferred feature of endoscope 10 to have the capability to control the optical environment within which it is imaging. Accordingly, endoscope 10 preferably includes a device 32 for altering the optical properties within the intravascular vessel in proximity to sensing region 14 and light source 16. Device 32 provides either one of two methods for altering the optical environment in order to enhance imaging: the first is to dilute the blood within the light path so that it less impedes the passage of light, and the second is to remove blood from the light path. In a preferred embodiment device 32 provides both methods and preferably variations thereof as well. The nature and function of device 32 for altering the optical properties will be discussed more fully hereinafter with respect to various embodiments of the invention.

Because device 32 disrupts the normal blood flow within the vascular vessel, endoscope 10 may preferably comprises a control unit 34 for operating device 32 in accordance with a predetermined procedure for balancing between visibility and non-interference with the blood supply, specifically, in order minimize disruption, consistent with the requirements of the imaging. Control unit 34 preferably carries out other control functions, such as coordinating data flow to and from camera 12 and light source 16 and carrying out commands from a processor remote from endoscope 10 regarding, for example, functions of sensing region 14 (AGC, integration time, etc.) shutter 22, light source 16 (movement, focus, intensity, etc.) and communication link 28. Control unit 34 may be a separate element situated at the distal head of endoscope 10, may be integrated with other components into a single semiconductor circuit or may be a part of the remote processor. The configuration of control unit 34 is not a material aspect of the invention.

It is appreciated that the internal configuration of endoscope 10 is not a material element of the present invention.

Endoscope 10 is associated with image processing functionality for providing images from light detected by sensing region 14. The image processing may be a physical process based upon the nature of the detected light according to the embodiment which employs polarized light, or upon different aspects of expected light reflection behavior, according to further embodiments of the invention, as follows:

a. expected light reflection behavior for light emitted from an internal wall surface within a continuous tubular structure. The expected behavior is superimposed upon actual received brightnesses in order to recognize and exclude reflected light that is not expected according to such behavior, and is more likely to come from the fluid than from the vascular wall;

b. expected light reflection behavior within a two directional pulse related intravascular fluid movement. The expected behavior is superimposed upon actual received brightnesses in order to recognize and exclude reflected light that is expected according to such behavior and which is therefore assumed to belong to the fluid; and c. expected light reflection behavior for light emitted within a pulse related radially expanding and contracting vascular vessel and reflected from the vessel wall which moves toward and away from sensing region 14. The expected behavior is superimposed upon actual received brightnesses in order to recognize and exclude light that is not expected according to such behavior as it is assumed to belong to the fluid.

Each of the bases of image processing functionality listed above will be fully described hereinafter with respect to one of the embodiments of the invention.

Endoscope 10 forms part of a diagnostic or therapeutic treatment system and may be used on catheters as a stand-alone viewing device or as part of a PTCA (Percutaneous Transluminal Coronary Angioplasty), stenting, laser, or any other cardiovascular operative or treatment device. However, it is appreciated that the application of endoscope 10 within an intravascular environment is only one of the possible applications. Minimally invasive surgery using endoscope 10 may be applied in many fields of medical diagnosis and therapy where imaging within an opaque medium is required, including but not limited to breast, urethral, renal, and abdominal environments.

It is an object of the embodiments to provide an enhanced photographic image of the internal vascular wall from within an intravascular environment. Imaging within such an environment is problematic because the ambient surroundings are blood, which has light disturbing properties. The primary disturbing factor of blood on the passage of light is scattering due to reflection from the many RBC's suspended within the blood. The scattered light does not contribute to the image but rather is a source of noise. Light reflected from the object of interest is considered signal. Increasing the amount of signal and reducing the amount of noise therefore results in a higher quality image.

Accordingly, the various embodiments of the invention are all directed, each in its specific way, to either reducing noise levels due to blood-induced scatter within the light path or overcoming the blood induced scatter effect within the light path. There are seven embodiments which may, for clarity, be divided into three categories, as follows:

a those relating to the intravascular environment, b. those relating to the emission of light, and c. those relating to the behavior of light.

The embodiments are not mutually exclusive and may be implemented without reference to the implementation of any other embodiment. It is a preferred embodiment of the invention to implement all or most of the embodiments simultaneously in order to gain the benefit of the image enhancing effects of each of them, thus providing a maximally enhanced image.

The embodiments are as follows:

Embodiments Relating to the Intravascular Environment.

1. Changing the Optical Properties of Blood

Blood is opaque in visible light illumination because blood contains suspended cells. This phenomenon is much like that encountered with water vapor drops in fog; even though the content of the red blood cells is transparent, when the content of red blood cells is arranged in "drops" surrounded by a membrane, the reflectance factor of the solution causes an opaque situation. Therefore, in order to obtain a clear vision of the field of view, one possibility comprises temporarily diluting the blood in the vicinity of any target region to be imaged. According to this embodiment, device 32 is a fluid injector for injecting a fluid into the intravascular environment in order to alter the optical properties of blood within the optical path of the emitted light, such that the blood provides less interference with the passage therethrough of the light.

There are a number of suitable fluids for injection. Such a fluid may be a fluid with a refraction factor identical or similar to the refraction factor of red blood cells, or a fluid that creates such a refraction factor when mixed in a certain concentration with blood. This type of fluid solves the problem of light scattering in blood, leaving only a light absorption problem, which is simpler to solve. Further types of fluid that may be used for dilution include fluids with a physiological concentration of particles and fluids with less than a physiological concentration of particles, such as 1/6 saline. The latter type of fluids can cause hemolysis of some of the red blood cells, thus improving the refraction factor of the blood, and reducing light scattering in blood. Another useful fluid is one capable of carrying oxygen, such as a blood substitute, which reduces the risk of hypoxia to the heart muscle caused by any extensive hemolysis of the red blood cells. Yet another useful fluid is one that enables a frequency conversion of light, e.g. from IR wavelengths to the visible light spectrum, thus making it possible to use a visible light sensing region 14 while retaining the advantages of illuminating with IR light. The fluid may be injected via catheter 24 or via any open channel 26.

The amount of injected fluid is preferably controlled by control unit 34 or may be controlled by a processor. The amount and timing of fluid injection may be determined according to the transparency level of the blood, as measured by light meter 30 indicating the level of reflection of illumination from light source 16 onto sensing region 14. Such variations in the amount and timing of fluid injection may be determined by a quality control algorithm, which may calculate necessary changes to fluid injection from the received information related to the optical environment.

Reference is made to FIG. 4, which shows a simple and representative algorithm for controlling the injection of fluid, in a process 40. Process 40 begins with step 41, injecting fluid into the blood in proximity to camera 12. Step 42 is to begin the imaging process. Light is emitted by light source 16 and reflected light is detected by sensing region 14. Step 43 includes collecting and measuring the light resulting in imaging data. Step 44 is to determine whether the imaging data meets or exceeds a predetermined threshold of resolution or other predetermined measure of quality, a process carried out by a processor with a logic circuit to compare data. If the answer is positive, the process moves to step 45, which is to continue the imaging. If the answer is negative, the process moves to step 46, which is to increase the injection of fluid. The next step is to return to step 43 by determining new imaging data. The next step is again step 44 to determine if the threshold is met. The yes or no answers result in the previously described continuation of the process.

Variations in the amount and timing of fluid injection may also be determined by the physiological condition of the subject. Disrupting the blood flow for the purpose of imaging must necessarily be balanced with the blood supply needs of the subject. Accordingly, control unit 34 and device 32 may be subject to control by a processor which receives data related to blood oxygen level or to other physiological factors so that a balance between visibility requirements for imaging and blood supply may be preserved without detriment to the subject.

The described embodiment is preferably used in combination with others of the disclosed embodiments.

2. Displacing Blood from the Light Path

Another manner of dealing with the opacity of blood is to simply displace the blood from the optical path of the emitted light during the emission period. One way of doing so is by placing a deployable transparent structure at the distal end of catheter 24. The structure is placed on the catheter either before or beyond light source 16 and sensing region 14.

The structure may be a flexible balloon, which inflates by having a transparent fluid or gas injected into it. The structure is deployed in its deflated mode and inflated whenever endoscope 10 is activated. When inflated, the balloon momentarily displaces the blood from the field of view. The structure may be a rigid dome, which is positioned around and at the edge of the distal end of catheter 24 extending distally. The rigid structure is situated so that it removes the blood from around light source 16 and sensing region 14, thus clearing the field of view between the dome and endoscope 10 without blocking the flow of blood in the vessel. The rigid structure may be either hollow or filled with a transparent fluid.

The structure may be deployed by the injection of a fluid or a gas via catheter 24 or via any open channel 26 in order to inflate the structure. Inflation is preferably controlled by a processor, and may be linked to the activation of endoscope 10 and, if necessary, to physiological parameters of the subject, such as blood pressure, heartbeat, etc. Such factors preferably determine the timing and the degree of the inflation of the balloon within the vessel.

Figure 5:
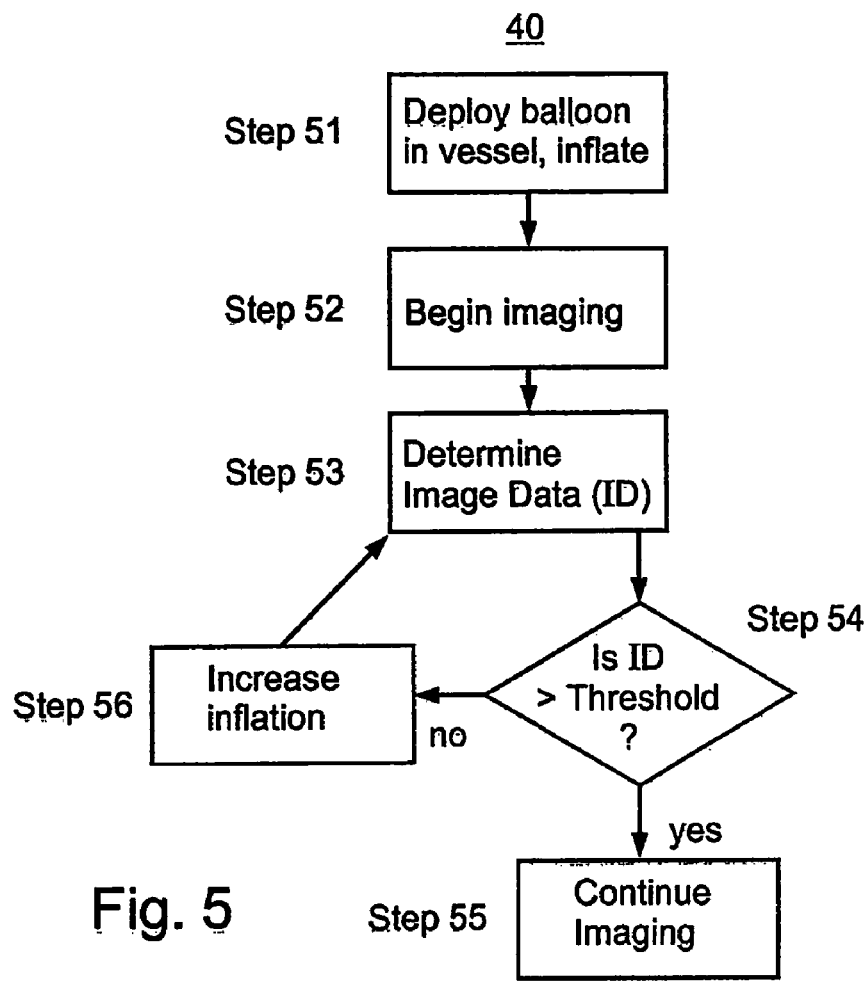

Variations in the amount and timing of inflation may be determined by a quality control algorithm, which may be able to calculate necessary changes to balloon inflation from the received information related to the optical environment. Reference is made to FIG. 5, which shows a simple and representative algorithm for controlling the inflation of the balloon.

Process 50 begins with step 51, deploying the balloon into the vessel and inflating it to a predetermined pressure. Step 52 is to begin the imaging process. Light is emitted by light source 16 and reflected light is detected by sensing region 14. Step 53 includes collecting and measuring the light resulting in imaging data Step 54 is to determine whether the imaging data meets or exceeds a predetermined threshold of resolution or other predetermined measure of quality, a process carried out by a processor with a logic circuit to compare data. If the answer is positive, the process moves to step 55, which is to continue the imaging. If the answer is negative, the process moves to step 56, which is to increase the inflation of the balloon. The next step is to return to step 53 by determining new imaging data. The next step is again step 54 to determine if the threshold is met. The yes or no answers result in the previously described continuation of the process.

It is well known in the art to inflate a balloon within a vascular vessel. It is further known in the art to inflate a balloon within a vein or artery in order to locally displace blood for the purpose of imaging therein. The described embodiment is disclosed in order to be used in combination with other of the disclosed embodiments and not as a separate invention.

Embodiments Relating to the Emission of Light

3. Emitting Polarized Light.

Light that impinges on a reflecting surface has a component that reflects, and in doing so undergoes polarization, the degree of polarization decreasing as the angle of incidence of the reflected light approaches the normal, and increasing as it approaches the perpendicular in relation to the reflecting surface. In an intravascular environment, light hitting the vessel wall, or any object connected or adjacent to the vessel wall, therefore reflects in a mostly polarized form, while the light hitting suspended cells in the blood is largely scattered and does not show any consistent polarization pattern. Because target regions to be imaged are typically the vessel wall or connected to the vessel wall, using polarized light for imaging provides a way of discriminating between the signal desired and extraneous noise. By emitting polarized light and polarization filtering the reflected light to remove non-polarized light and light polarized at undesirable angles, the detected light will be only, or largely, properly polarized light, i.e. the light reflected from the target object of interest. This method of using polarized light and a polarizing filter increases the signal/noise ratio of the detected light and therefore improves the quality of the reconstructed image.

This present embodiment includes four elements:

A. The use of a polarized light source 16 for illumination. Light is rotated when reflected from a solid object, as explained above. Therefore, light polarized at a specific angle will all be similarly rotated to a new angle when reflected from the same object. Light reflected from extraneous objects, such as red blood cells, will also be rotated, but not to the same angle. The embodiment may use two polarized light sources 16, which preferably, but not necessarily, emit light at polarization angles perpendicular to each other. There may be a plurality of light sources 16 with typically half emitting light at a certain polarization angle and the other half emitting light at a perpendicular polarization angle. There also may be a combination of light sources 16 with more than two polarization angles. Light sources 16 may emit light of different wavelengths, including visible light, IR and UV or any combination thereof. Light sources 16 may be coherent or incoherent sources.

B. Disposing a polarizing filter 20 on the light return path such that light reflected from the object of interest passes therethrough before being detected by sensing region 14. The orientation of filter 20 is correlated to the polarization angles of the light. The filters may be positioned at any point on the light path, but a preferable disposition is adjacent to sensing region 14.

With respect to configurations in which multiple light sources 16 are employed, endoscope 10 may be configured with multiple sensing regions 14 and multiple filters 20, each filter 20 being associated with and filtering light detected by one specific sensing region 14. According to another configuration of the present invention, reference is again made to FIG. 2 which depicts sensing region 14 divided into pixels of light, and to FIG. 3, which depicts filter 20 divided into separately oriented filtering regions, each one being associated with one pixel of sensing region 14. A further configuration includes dividing sensing region 14 into segments, with a different filter 20 over each segment.

Having multiple light sources, sensing regions and filters provides a wider range of receptivity to the signal, i.e., desirably polarized reflected light. It is likely that the polarization angle of the light will not match the exact orientation of the filter. However, if there are two filters oriented perpendicularly to one another, a portion of the reflected light may be filtered out by each of the filters. Therefore, if the desired polarization angle of the reflected light is, for example, at forty five degrees to the orientation of the filters, each filter may be configured to compare the light that reaches it and to pass through light that is equally proportioned between the two filters, which is thus recognized as the signal, and to filter out light that is not equally proportioned between the two filters, which is thus recognized to be noise.

C. Alternately flashing the two or more different polarized light sources 16. A further effect may be achieved by using polarized light sources in different wavelengths and filters in accordance with these wavelengths. In this case, the illumination from the different light sources may be projected simultaneously and provide spectrometric information in order to reconstruct the color of the objects of interest.

D. An algorithm designed to calculate statistical parameters of the Signal and Noise for each light projection and to use this information to improve the S/N ratio.

The above four elements combine in the following simplified example which illustrates how polarized light emitted from a vertically polarized light source and from a horizontally polarized light source may be used to improve the signal/noise ration in order to enhance the reconstruction of an image from optical data. Reference is again made to FIG. 2 which shows sensing region 14 pixilated into areas that detect one pixel of light, V indicating areas that detect vertically polarized pixels and H indicating areas that detect horizontally polarized pixels. Each pixel is associated with a separately oriented filtering region, and the arrangement of the filtering regions is V/H interspersed, as shown in FIG. 3.

Figure 6A:
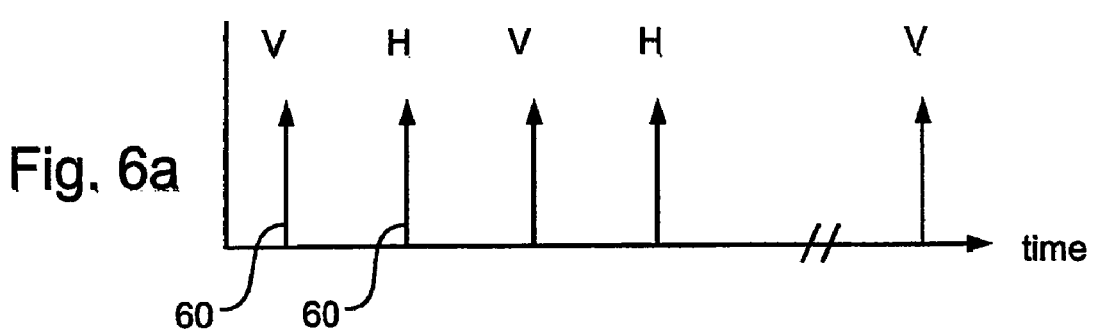
FIGS. 6a and 6b are graphic representations of the time related distinguishment of detected light between the sought signal and surrounding noise.
Figure 6B:
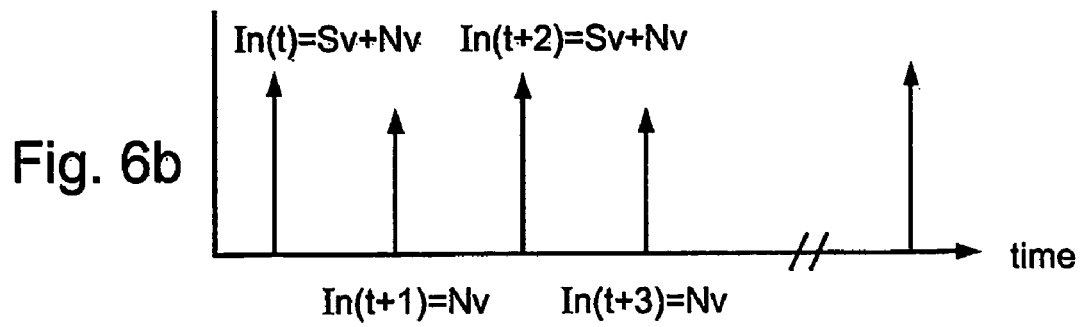

Reference is now made to FIG. 6a which is a graphic representation of the switching in time between the two light sources, each vertical arrow 60 indicating either a vertically polarized illumination flash or a horizontally polarized illumination flash along a time continuum. FIG. 6b is a graphic representation of the components of light detected by a "V" pixel with each illumination flash, both from the vertical and horizontal light sources.

During illumination by the vertical light source at a point (t) in time, the Detection by the vertical pixel can be described by the formula: $IN_{(t)} = Sv_{(t)} + Nv_{(t)}$, in which In = the amount of light detected by the pixel in a point in time (t, t+1, . . . , t+n) according to the time of illumination;

Sv = The part of the detected light that is the Signal, i.e. light from the vertical light source reflected from the object of interest; and Nv = The part of the detected light that is the Noise, i.e. light from one of two sources: (a) the vertical light source/light reflected from any object in the field other than the object of interest and yet reflected back vertically polarized, or (b) the horizontal light source/light reflected from any object in the field which changed its polarization to vertical.

During illumination by the horizontal light source at a point (t+1) in time, the detection by a vertical pixel can be described as: $In_{(t+1)} = Nv_{(t+1)}$. During the next illumination by the vertical light source at a point (t+2) in time, the detection is described as $In_{(t+2)} = Sv_{(t+2)} + Nv_{(t+2)}$, and so on. Therefore, in order to extract from the series of illuminations only the detected light which represents the signal, the following calculation is preferably made:

$Sv_{(t)} = In_{(t)} - In_{(t-1)}$ $Sv_{(t+1)} = In_{(t)} - In_{(t+1)}$ $SV_{(t+2)} = In_{(t+2)} - In_{(t+1)}$ $SV_{(t+3)} = In_{(t+2)} - In_{(t+3)}$ $SV_{(t+2*N=1)} In_{(t+2*N)} - In_{(t+2*N-1)}$ $SV_{(t+2*N+1)} = In_{(t+2*N)} - In_{(t+2*N+1)}$ (N=any natural number)

4. Emitting Light Restricted to a Limited Field.

In a preferred embodiment of the present invention, light source 16 is controlled to emit light to impinge upon a predetermined limited field which includes the target region but substantially excludes surroundings of the target region. In this way, surrounding-induced reflected light, often a substantial contribution to the overall noise, is reduced, resulting in an improved signal/noise ratio.

Figure 7:
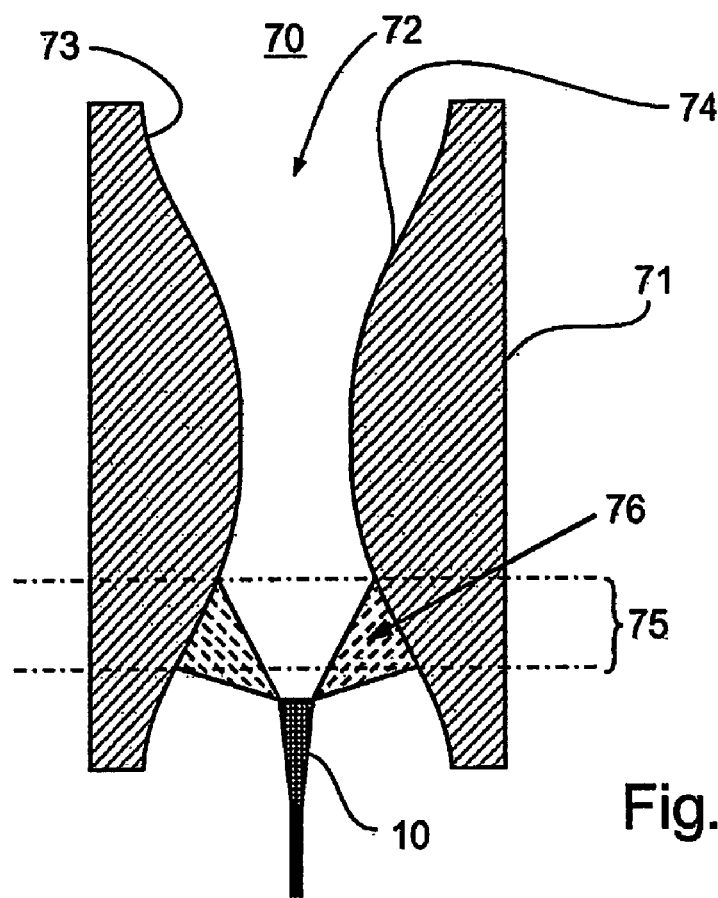
FIG. 7 is a schematic illustration of a longitudinal section of a vascular vessel with the apparatus of FIG. 1 disposed therein.

This embodiment is demonstrated by reference to FIG. 7, which is a schematic illustration of a longitudinal section of a vascular vessel 70 with endoscope 10 disposed therein. Shown is the exterior vessel wall 71, the lumen of the vessel 72, the interior vessel wall 73 and a bulge 74 on interior wall 73. Bulge 74 is the object of interest. As can be seen, a small segment of bulge 74 is the area of interest 75 for imaging. Accordingly, endoscope 10 is controlled to emit a narrow beam from a light source, not shown, which is focused to illuminate only illumination area 76.

The described embodiment is preferably used in combination with others of the disclosed embodiments.

Embodiments Relating to the Behavior of Light

5. Reconstructing an image from detected light based upon expected light reflection behavior for light emitted within a continuous tubular structure in order to recognize and exclude reflected light that is not expected according to the expected behavior.

The present embodiment is intended to provide images of the inner wall of an intravascular vessel which is essentially tubular in structure. A model can be constructed to describe light reflection behavior within a continuous tubular structure under point illumination pattern. Light is reflected from the interior wall of the vessel and the intensity of the light reflected can be shown to be a factor of certain parameters of the tubular environment and its relationship to the light source. Such a model makes it possible to discern which detected light is reflected from the vessel wall, as such light generally conforms to the model. On the other hand detected light which is reflected from other target regions, such as red blood cells, typically deviates from the model. As the target region of the imaging is typically the interior wall itself or an object connected to or adjacent to the interior wall, the light reflected from the interior wall or from an object adjacent to it is thus considered signal while light reflected from other objects forms the noise. In the present embodiment, image reconstruction is thus based upon using such a point illumination model, and thereafter measuring real-time detected brightnesses against the model to discriminate between signal and noise, and excluding the noise.

Figure 8:
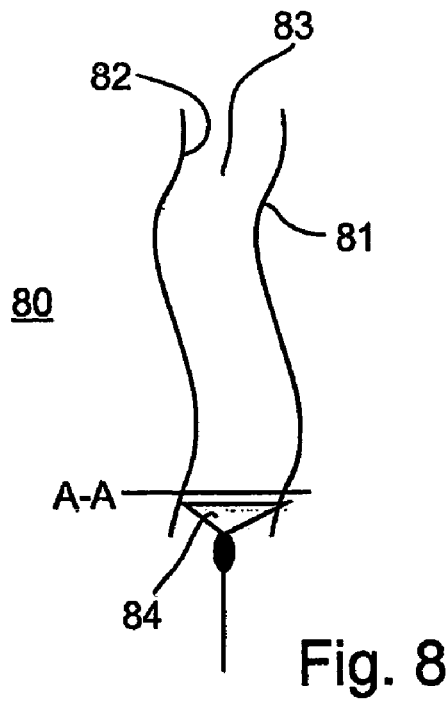
FIG. 8 is a schematic illustration of a longitudinal section of a vascular vessel with the apparatus of FIG. 1 disposed therein.
Figure 9:
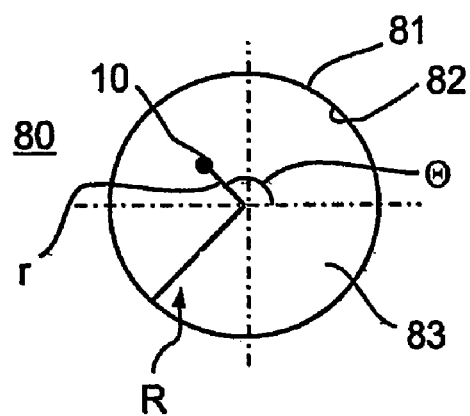
FIG. 9 is a schematic illustration of a radial section of a vascular vessel with the apparatus of FIG. 1 disposed therein.

In order to illustrate the creation and subsequent calibration of an appropriate light illumination model, reference is made to FIG. 8, which is a schematic illustration of a longitudinal section of a vascular vessel 80 with endoscope 10 disposed therein. Shown is the exterior wall 81, the interior wall 82, and the lumen 83 of vessel 80. The emitted light field 84 emanates from endoscope 10 which is disposed within lumen 83. Section designation A-A refers to FIG. 9, which is a schematic illustration of a radial section of vessel 80 at plane A-A, also shown with endoscope 10 disposed therein.

The parameters upon which the point illumination pattern is based, and which define the tubular structure and its relation to the light source, include a distance from light source 16 to the radial center of vessel 80, which is designated "r"; the radius of vessel 80, which is designated "R"; and the angle between a radial line from the radial center of vessel 80 to light source 16 and a radial line from the radial center of vessel 80 to the object of interest, which is designated "θ". As each of these parameters varies, so does the illumination implied by the model.

Image reconstruction according to the present embodiment firstly requires calibrating the model, that is to say determining the most accurate parameter values Once the model has been calibrated, the same parameter values will be used to judge real-time detected brightnesses in order to determine whether they conform to the pattern or deviate from it, i.e. whether it is signal or noise.

As in previous embodiments, the evaluation of the detected light and the determination whether to include it in the image reconstruction or to exclude it is carried out by the processor running the image reconstruction function. The determination is preferably based upon a simple comparative logic circuit programmed to discard light that momentarily or irregularly deviates from the predefined pattern and to retain light that either conforms to the pattern or that is within an acceptable deviation definition, such as a series of similar deviations or deviations of a certain amplitude.

Figure 10A:
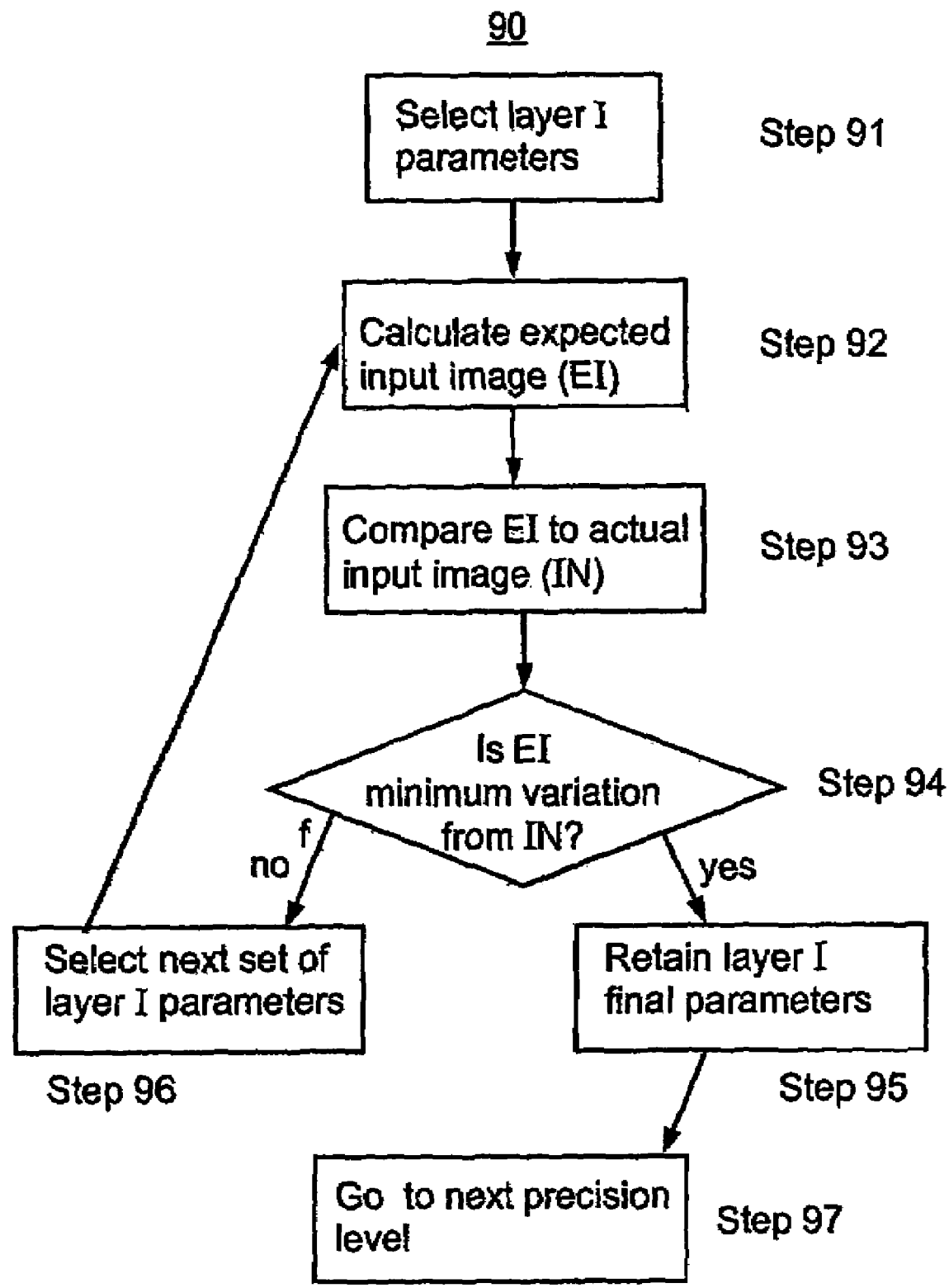
FIGS. 10*a* and 10*b* are flow diagrams respectively illustrating a first phase and a second phase of an image reconstruction algorithm usable in accordance with a number of embodiments of the present invention.
Figure 10B:
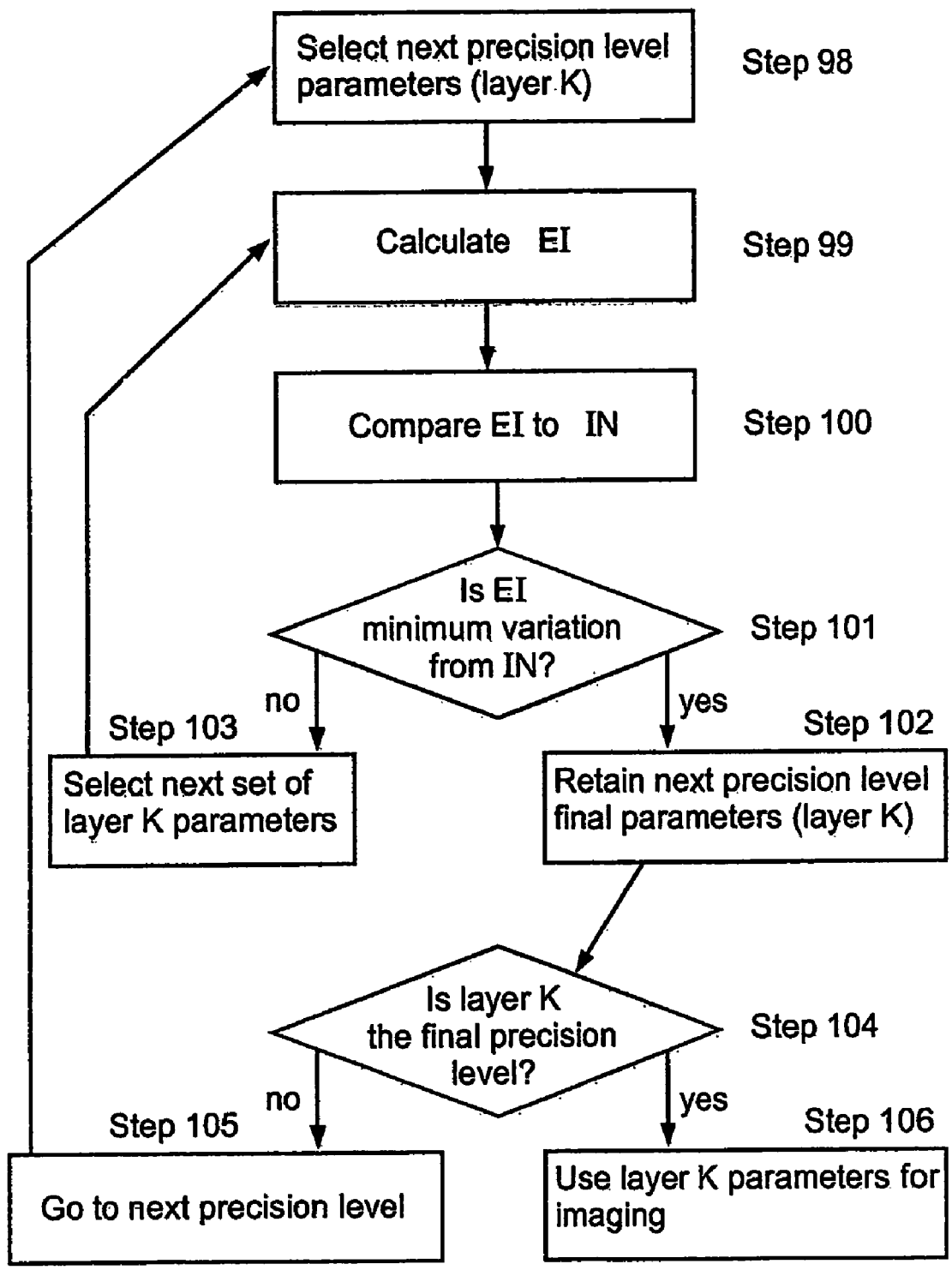

The most accurate set of parameter values is determined by a process of refinement according to an algorithm. Reference is now made to FIGS. 10a and 10b which are flow diagrams respectively illustrating a first phase and a second phase of an algorithm usable to determine parameter values for creating a point illumination pattern appropriate to the tubular structure. The algorithm is carried out by a processor, which receives imaging data from endoscope 10 deployed in vessel 80. In order to carry out the algorithm, it is assumed that interior wall 82 is a continuous surface and that the geometrical parameters of "r", "R" and "θ" do not vary significantly. All possible patterns of intensity of the reflected light from the vessel wall can be determined from this limited range of parameters.

The algorithm is for the purpose of calibrating the model, that is to say determining a set of parameters to apply to the model to best describe illumination levels actually obtained in a calibration image capture. Once the most accurate set of parameter values is determined, a point illumination pattern may be created from the model to be used for real-time imaging to determine which detected light conforms to the pattern and is to be included in the reconstruction of the image (signal) and which deviates from the pattern and is to be excluded (noise).

The initialization phase 90 begins at the lowest level of precision, shown as layer I, with step 91, which initially selects values for $R_1$, $r_1$ and $\theta_1$. Step 92 uses the selected parameter values to calculate an expected input image (EI). Step 93 compares the EI to the actual input image (IN). Step 94 determines if the EI represents the minimum variation from the IN at the current layer of precision. If the EI does in fact represent the minimum variation, Step 95 retains the parameter values for $R_1$, $r_1$, and $\theta_1$. If the EI does not represent the minimum variation, Step 96 then selects a different combination of parameter values for $R_1$, $r_1$, and $\theta_1$ and repeats the sequence of steps 91 through 94 to determine if the EI produced represents the minimum variation from the IN for the new set Different combinations are selected and tested until a set of values is found that represents the minimum variation between EI and IN.

Once the most accurate set of parameter values is found, the algorithm continues to step 97 in order to further refine the values by upgrading to a higher level of precision, referred to hereinafter as level "k". The "k" level of precision is shown in FIG. 10b and begins with step 98, which involves perturbing the values from the previous level for $R_k$, $r_k$, and $\theta_k$. Perturbations are assigned by selecting an arbitrary deviation value delta, to the previous level's final values of $R_1$, $r_1$, and $\theta_1$. Different perturbed combinations are arrived at by randomly adding, subtracting or zeroing deltas to the different parameters. Typically the deltas may be ten percent of the parameter values or delta values of the previous level. The new values $R_k$, $r_k$, and $\theta_k$ are therefore respectively selected from the ranges $R_{k-1}$–delta to $R_{k-1}$+delta, $r_{k-1}$–delta to $r_{k-1}$+delta, and $\theta_{k-1}$–delta to $\theta_{k-1}$+delta.

Once a new set of parameter values is assigned from within the described ranges, step 99 is to calculate the expected input image (EI) for the current set of parameter values. Step 100 compares the EI to the actual input image (IN). Step 101, corresponding to former step 94, determines if the EI represents the minimum variation from the IN according to the k layer of precision. If the EI does in fact represent the minimum variation, step 102 retains the parameter values for $R_k$, $r_k$, and $\theta_k$. If the EI does not represent the minimum variation, Step 103, corresponding to former step 96, selects a different combination of parameter values for $R_k$, $r_k$, and $\theta_k$ from within the range of plus delta and minus delta and repeats the sequence of steps 98 through 101 to determine if the EI produced by these new parameter values represent a predetermined minimum variation from the IN. If it does not, the selection of different combinations of parameter values from within the k level of precision continues until a set of perturbed parameter values having the minimum variation is found.

The algorithm then continues to step 104 which is to ask whether layer k is the final precision level. If it is not, step 105 is to upgrade to a higher level of precision by selecting another size of delta with which to perturb the parameter values as finally accepted in the former precision level. The delta may preferably be ten percent of the delta of the previous level. Thereafter, steps 98-104 of the algorithm are repeated at this new precision level until final parameter values are found which represent the minimum variation between EI and IN at the new and higher level of precision.

An arbitrary final level of precision is selected based upon the degree of accuracy desired for the image reconstruction process, and the algorithm ends at step 106 when parameter values are found that represent the minimum variation between EI and IN at the final level of precision. The corresponding set of parameter values are then used as the calibrated model with which to discriminate between signal and noise in the real time imaging.

6. Reconstructing an image from detected light based upon expected light reflection behavior for light emitted within a two directional pulse related intravascular fluid movement in order to recognize and exclude reflected light that corresponds to the expected behavior. That is to say the embodiment has a model of brightness behavior that describes a point moving in a pulsed fluid past a point illumination source. Any point whose brightness changes in accordance with that model is assumed to belong to the fluid and is excluded from the final image as noise.

The present embodiment is intended to discriminate between signal and noise when detecting light within an intravascular vessel which has within it a discontinuous or pulsed flow of blood. Accordingly, brightness levels for particles in the fluid may be modeled by applying a formula similar to that for the wall of the tube and additionally taking the fluid movement into account to describe periodic changes in the particle's brightness. Such changes can be detected and can be described as the expected reflection behavior of light reflected from RBCs.

Based upon such a model, it is possible to discern which light is reflected from the vessel wall and which light is reflected from RBCs. Therefore, the image reconstruction of the present embodiment is based upon a similar process as described with respect to the former embodiment, however the light detected which conforms to the expected behavior of light reflected from RBCs is recognized as noise and excluded.

Image reconstruction according to the present embodiment is also based upon applying the most accurate set of parameter values to detected light in order to create the appropriate light intensity pattern and to determine if the detected light conforms to or deviates from the pattern Accordingly, the algorithm described in FIGS. 10a and 10b is equally applicable to the present embodiment for these purposes and the previous discussion about determining optimal parameter values, creating the pattern, and judging real-time detected light is equally applicable with respect to the present embodiment and need not be repeated, with the proviso that the particles in the blood are not all at the same radius, so that calibration is not possible with respect to absolute brightness values but only to rates of change of the brightness values with motion. With respect the present embodiment, the detected light that conforms to the expected behavior for light emitted within such a fluid movement and reflected from the RBCs is considered noise and is excluded and the light that deviates from this expected behavior is considered signal and is included in the image reconstruction.

Moreover, as in the former embodiment, the algorithm is preferably carried out by the processor running the image reconstruction function. The processor thus also determines which detected light is signal and which is noise based upon the same kind of comparison with the model, but this time programmed to retain light that deviates from the predefined pattern and to exclude light that conforms to the pattern.

The present embodiment is further capable of effectuation based upon physiological coordination with the heartbeat of the subject As the movement of RBCs is correlated to the heartbeat, endoscope 10 may further comprise a heartbeat monitor such as a plethysmograph or other sensing device that may be connected to the subject's body from outside or may be insertable into the vessel with catheter 24. The monitor may preferably transmit data regarding the heartbeat to a processor associated with endoscope 10 to control light source 16 to emit light in time sequential flashes coordinated with the pulse so that light is emitted at a constant point of the heart contraction cycle, preferably when the blood pauses its forward movement as a result of the contraction and before its reverse movement as a result of the release of pressure from the previous contraction. Such coordination will cause the RBCs to be in the same condition with respect to movement at each emission of light. Accordingly, a variation in reflected light behavior caused by the pulse related two-way movement of the blood may be avoided in this manner.

7. Reconstructing an image from detected light based upon expected light reflection behavior for light emitted within a pulse related radially expanding and contracting vascular vessel in order to recognize and exclude reflected light that is not expected according to the expected behavior. That is to say, a model is constructed of brightness variation behavior expected from the vascular wall given that it moves in and out in accordance with the pulse. Points of light in the raw image that conform to the model are assumed to belong to the vascular wall and are retained as signal. Points of light that do not conform to the model are assumed to be noise and are excluded.

The present embodiment attempts to discriminate between signal and noise when detecting light within a pulsing vascular vessel. Such a vessel has an internal pressure which vacillates with the heartbeat causing it to periodically expand and contract radially. Accordingly, a model of expected light reflection behavior within such an expanding and contracting vessel will be expressed by the customary light intensity pattern for light reflected from the interior wall of the vessel, but will vary periodically as a result of the vessel wall moving toward and away from the light source. Accordingly, the light intensity pattern shows a periodically increasing and decreasing intensity of light which appears as recurring variations in the pattern. Such variations can be detected and expressed in the light intensity pattern as a function of time.

Such a pattern describes the expected reflection behavior of light emitted within a tubular vessel which periodically varies between a radially expanded condition and a radially contracted condition. Therefore, the image reconstruction of the present embodiment is based upon such a variable pattern and employs a similar process to judge real-time detected light as is described with respect to the former embodiment. However, the light detected which does not conform to the expected behavior is excluded for image reconstruction.

Image reconstruction according to the present embodiment is also based upon applying the most accurate set of parameter values to detected light in order to create the appropriate light intensity pattern and to determine if the detected light conforms to or deviates from the pattern. Accordingly, the parameters identified in FIGS. 8 and 9 and the algorithm described in FIGS. 10a and 10b are equally applicable to the present embodiment for these purposes and the discussion of determining optimal parameter values, creating the pattern, and judging real-time detected light is equally applicable with respect to the present embodiment and need not be repeated. However, with respect to the present embodiment, the detected light that does not conform to the expected behavior for light emitted within a radially expanding and contracting vessel is considered noise and is excluded and the detected light that conforms to the expected behavior is considered signal and is included. Moreover, as in the former embodiment, the algorithm is preferably carried out by the processor running the image reconstruction function, which may then determine which detected light is signal and which is noise based upon the same comparison between the model and the actual behavior of given brightness points.

The present embodiment is further capable of effectuation based upon physiological coordination with the heartbeat of the subject. As the expansion and contraction of the vessel is correlated to the heartbeat, endoscope 10 may further comprise a heartbeat monitor, not shown, which may be associated with endoscope 10 in order to control light source 16 to emit light in time sequential flashes coordinated with the subject's pulse so that light is emitted at a constant point within the heartbeat cycle. Such coordination causes the vessel to be in the same expanded/contracted condition with respect to each emission of light and thereby avoid the effect of the expansion and contraction on the reflected light Accordingly, a variation in reflected light behavior caused by the pulse related expansion and contraction of the vessel may be avoided in this manner.

It is appreciated that each of the above embodiments, and any variations of such embodiments, may be implemented irrespective of the implementation of any other of the described embodiments. Each embodiment has an image enhancing effect due to its effect on the optical environment, on the emitted light or on the detection of reflected light and each one improves resolution of the reconstructed image by eliminating or reducing a form of noise, thus improving the signal/noise ratio.

Reference is now made to FIG. 11 which is a schematic illustration of a system 100 for providing an image within an intravascular environment in accordance with an embodiment of the present invention. Shown is endoscope 10 along with a range of elements external to endoscope 10 which together comprise system 100. Insofar as system 100 comprises elements internal to endoscope 10 shown in FIG. 1, elements of endoscope 10 described with respect to system 100 have the same reference number as cited in FIG. 1 and the description of such elements will not be repeated. Moreover, insofar as system 100 comprises elements that are also described hereinbefore with respect to endoscope 10, the description is herewith incorporated by reference thereto and is not repeated.

System 100 includes endoscope 10 comprising camera 12 having a light sensing region 14 for detecting light and a light source 16 for emitting light to impinge upon the target region. Light source 16 may preferably, but not necessarily, emit polarized light, in which case system 100 further comprises a polarization filter 20 for polarization filtering reflected light. Light source 16 is preferably controlled to emit light to impinge on a predetermined area which includes the target region and which substantially excludes the target region's surroundings. Endoscope 10 also comprises a light meter 30 for measuring the optical properties within the intravascular environment in proximity to sensing region 14 and light source 16, a device 32 for altering the optical properties within the vascular vessel in proximity to camera 12 along with a control unit 34 for operating device 32, and a communication link for conveying data to and from endoscope 10.

System 100 also preferably comprises a graphic user interface 102 which preferably includes controls for entering user commands and a visual display for displaying images of the target region.

System 100 also preferably comprises a processor 104 external to endoscope 10 for receiving data related to the optical environment within the vascular vessel; for using the data to determine at least one optical requirement for imaging within the vessel; for determining operational commands to carry out actions needed in order to control camera 12, light source 16 or the optical environment within the vessel; and for receiving data associated with light detected by sensing region 14.

Processor 104 is also for carrying out image processing functionality for reconstructing images from light detected within the vessel. The reconstruction may be based upon expected light reflection behavior for light emitted within a continuous tubular structure in order to recognize and exclude reflected light that is not expected, and/or it may be based upon expected light reflection behavior within a two directional pulse related movement of blood in order to recognize and exclude reflected light that is expected, or it may be based upon expected light reflection behavior for light emitted within a pulse related radially expanding and contracting vascular vessel in order to recognize and exclude light that is not expected. System 100 may preferably have any or all capabilities of providing an image of a target region within a vascular vessel as are hereinbefore described with respect to endoscope 10 and may include any or all of the embodiments of endoscope 10 hereinbefore described.

System 100 also preferably comprises a communication unit 106 for conveying optical data to processor 104, for conveying operational commands to endoscope 10, for conveying data from endoscope 10 to processor 104, and for conveying data representing a reconstructed image to a viewable location. System 100 also comprises a guide member 24 for inserting endoscope 10 into the vessel, which is preferably a catheter having at least one open channel 26.

Moreover, system 100 may further be equipped with a range of documentation and storage capabilities such as a printer to print documents and image, along with an image enhancement software package for producing high quality hard copies of images. It may also comprise a VCR for recording video images and a digital storage device for archiving videos.

Reference is now made to FIG. 12 which is a flow diagram illustrating a method 110 of providing an image in accordance with the embodiment of endoscope 10 in which polarized light is used to enhance imaging. It is understood that each of the steps of method 110 hereinafter described, and of further methods hereinafter described, refer to endoscope 10 and the elements thereof and likewise to system 100.

Method 110 begins with a step 111 of inserting endoscope 10 into the vascular vessel in proximity to the target Step 112 is to emit polarized light from light source 16 to impinge upon the target region. Step 113 is polarization filtering the light after at least some of the light is reflected from the target region, and step 114 is detecting the polarization filtered light. As described hereinbefore with respect to an embodiment of endoscope 10, the polarization filtering removes a portion of the light not usable for image reconstruction and therefore prepares for step 115, which is reconstructing an image based upon the detected polarization filtered light.

It is understood that method 110 may also include further steps not shown in FIG. 12, such as reconstructing an image from the detected light based upon expected light reflection behavior for light emitted within a continuous tubular structure or within a two directional pulse related intravascular fluid movement or within a pulse related radially expanding and contracting vascular vessel; emitting the polarized light to impinge upon a predetermined field including the target region and substantially excluding surroundings of the target region; conveying data representing a reconstructed image of the target region to a viewable location; providing for graphical user interfacing including providing graphical controls for entering user commands and displaying a reconstructed image; and altering optical properties within the vascular vessel in proximity to endoscope 10.

Reference is now made to FIG. 13, which is a flow diagram illustrating a method of providing an image in accordance with the embodiment of endoscope 10 in which light is emitted to impinge upon a predetermined field including the target region and substantially excluding surroundings of the target region, hereinafter referred to as method 120.

Method 120 begins with a step 121 of inserting endoscope 10 into the vascular vessel in proximity to the target. Step 122 is to emit light, either polarized or unpolarized, from light source 16 to impinge upon a predetermined field including the target region and substantially excluding surroundings of the target region. Step 123 is detecting the light after at least a portion has been reflected from the target region. Step 124 is reconstructing an image based upon the detected light.

It is understood that method 120 may also include further steps not shown in FIG. 13, such as reconstructing an image from the detected light based upon expected light reflection behavior for light emitted within a continuous tubular structure or within a two directional pulse related intravascular fluid movement or within a pulse related radially expanding and contracting vascular vessel; conveying data representing a reconstructed image of the target region to a viewable location; providing for graphical user interfacing including providing graphical controls for entering user commands and displaying a reconstructed image; and altering optical properties within the vascular vessel in proximity to endoscope 10.

Figure 14:
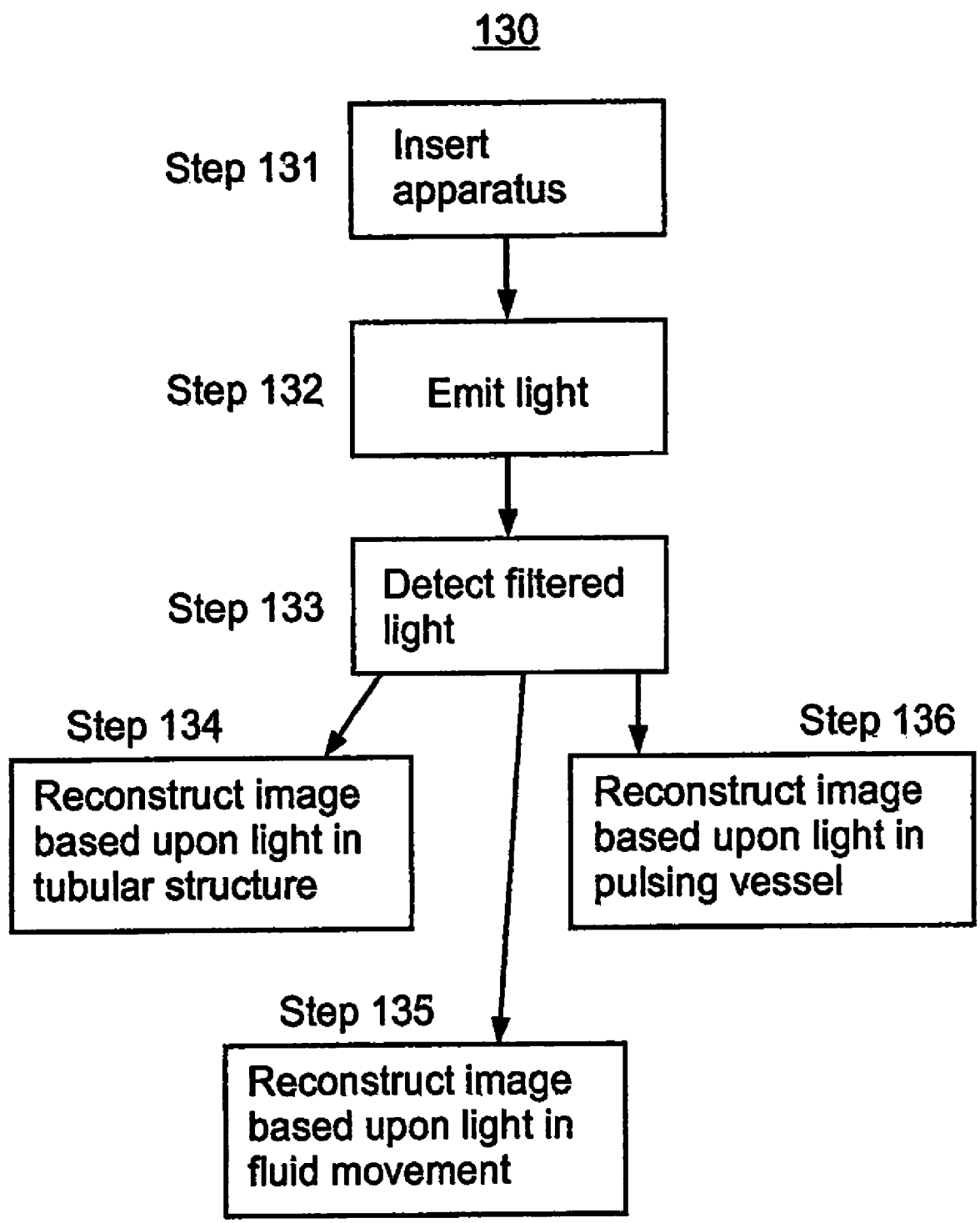
FIG. 14 is a flow diagram illustrating a further preferred embodiment of a method for providing an image in accordance with the present invention.

Reference is now made to FIG. 14 which is a flow diagram illustrating a method of providing an image in accordance with the embodiments of endoscope 10 in which images are reconstructed from the detected light based upon expected light reflection behavior for light emitted within a continuous tubular structure or within a two directional pulse related intravascular fluid movement or within a pulse related radially expanding and contracting vascular vessel, hereinafter referred to as method 130.

Method 130 begins with a step 131 of inserting endoscope 10 into the vascular vessel in proximity to the target. Step 132 is to emit light, either polarized or unpolarized, from light source 16 to impinge upon the target region. Step 133 is detecting the light after at least a portion has been reflected from the target region. Step 134 is reconstructing an image based upon expected light reflection behavior for light emitted within a continuous tubular structure or within a two directional pulse related intravascular fluid movement or within a pulse related radially expanding and contracting vascular vessel.

It is understood that method 130 may also include further steps not shown in FIG. 14, such as emitting light to impinge upon a predetermined field including the target region and substantially excluding surroundings of the target region; conveying data representing a reconstructed image of the target region to a viewable location; providing for graphical user interfacing including providing graphical controls for entering user commands and displaying a reconstructed image; and altering optical properties within the vascular vessel in proximity to endoscope 10.

It is appreciated that methods 110, 120 and 130 described above and hereinafter claimed reflect the use of the hereinbefore described embodiments of endoscope 10 and system 100 and such methods are intended to encompass all uses and implementations thereof.

Additional objects, advantages, and novel features of the present invention will become apparent to one ordinarily skilled in the art upon examination of the following examples, which are not intended to be limiting; Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A system for providing an image of a target region located within an intravascular environment, said system comprising: an imaging apparatus comprising
   a. a camera having at least one light sensing region for detecting light, the sensing region being located within a portion of the apparatus inserted into the intravascular environment;
   b. at least one light source for emitting polarized light to impinge upon said target region, the light source being positioned and oriented along an insertion end of the apparatus so that at least a portion of the light that it emits is reflected by the target region to be detected by the sensing region;
   c. at least one polarization filter for polarization filtering said light, said filter being disposed on the light path such that light reflected from said target region passes through said filter before being detected by said light sensing region; and
   d. the system further comprising a processor and stored instructions for implementing an algorithm for reconstruction of at least one image from light detected by the light sensing region, the reconstruction being based upon the detected polarization filtered light; and
wherein the stored instructions for reconstruction of at least one image from light detected by said light sensing region further comprise an algorithm based upon expected light reflection behavior for light emitted within a continuous tubular structure in order to recognize and exclude reflected light that is not expected according to said behavior; and wherein the stored instructions include an algorithm implementing a point illumination model for a continuous tubular structure.

2. A system for providing an image of a target region located within an intravascular environment, said system comprising: an imaging apparatus comprising
   a. a camera having at least one light sensing region for detecting light, the sensing region being located within a portion of the apparatus inserted into the intravascular environment;
   b. at least one light source for emitting polarized light to impinge upon said target region, the light source being positioned and oriented along an insertion end of the apparatus so that at least a portion of the light that it emits is reflected by the target region to be detected by the sensing region;
   c. at least one polarization filter for polarization filtering said light, said filter being disposed on the light path such that light reflected from said target region passes through said filter before being detected by said light sensing region; and
   d. the system further comprising a processor and stored instructions for implementing an algorithm for reconstruction of at least one image from light detected by the light sensing region, the reconstruction being based upon the detected polarization filtered light; and
wherein the stored instructions for reconstruction of at least one image from light detected by said light sensing region further comprise an algorithm based upon expected light reflection behavior within a two directional pulse related intravascular fluid movement in order to recognize and exclude reflected light that is expected according to said behavior; and wherein the stored instructions include a brightness behavior model for a point moving in a pulsed fluid past a point illumination source.

3. A system for providing an image of a target region located within an intravascular environment, said system comprising: an imaging apparatus comprising
   a. a camera having at least one light sensing region for detecting light, the sensing region being located within a portion of the apparatus inserted into the intravascular environment;
   b. at least one light source for emitting polarized light to impinge upon said target region, the light source being positioned and oriented along an insertion end of the apparatus so that at least a portion of the light that it emits is reflected by the target region to be detected by the sensing region;
   c. at least one polarization filter for polarization filtering said light, said filter being disposed on the light path such that light reflected from said target region passes through said filter before being detected by said light sensing region; and
   d. the system further comprising a processor and stored instructions for implementing an algorithm for reconstruction of at least one image from light detected by the light sensing region, the reconstruction being based upon the detected polarization filtered light; and
wherein the stored instructions for reconstruction of at least one image from light detected by said light sensing region further comprise an algorithm based upon expected light reflection behavior for light emitted within a pulse related radially expanding and contracting vascular vessel in order to recognize and exclude light that is not expected according to said behavior; and wherein the stored instructions for reconstruction include a model of brightness variation behavior expected from a vascular wall given that the vascular wall moves in and out in accordance with a pulse.

4. A system for providing an image of a target region located within an intravascular environment, said system comprising: an imaging apparatus comprising
   a. a camera having at least one light sensing region for detecting light, the sensing region being located within a portion of the apparatus inserted into the intravascular environment;
   b. at least one light source for emitting polarized light to impinge upon said target region, the light source being positioned and oriented along an insertion end of the apparatus so that at least a portion of the light that it emits is reflected by the target region to be detected by the sensing region;
   c. at least one polarization filter for polarization filtering said light, said filter being disposed on the light path such that light reflected from said target region passes through said filter before being detected by said light sensing region; and
   d. the system further comprising a processor and stored instructions for implementing an algorithm for reconstruction of at least one image from light detected by the light sensing region, the reconstruction being based upon the detected polarization filtered light; and
wherein said at least one light source is controllable to emit said light to impinge upon a predetermined field including said target region and substantially excluding surroundings of said target region, thereby to reduce surrounding-induced reflected light from being detected by said light sensing region; and wherein the stored instructions for reconstruction of at least one image from light detected by said light sensing region further comprise an algorithm based upon expected light reflection behavior for light emitted within a continuous tubular structure in order to recognize and exclude reflected light that is not expected according to said behavior, wherein the stored instructions for reconstruction include a point illumination model for a continuous tubular structure; and further based upon expected light reflection behavior within a two directional pulse related intravascular fluid movement in order to recognize and exclude reflected light that is expected according to said behavior, wherein the stored instructions for reconstruction include a brightness behavior model for a point moving in a pulsed fluid past a point illumination source; and further based upon expected light reflection behavior for light emitted within a pulse related radially expanding and contracting vascular vessel in order to recognize and exclude light that is not expected according to said behavior, wherein the stored instructions for reconstruction include a model of brightness variation behavior expected from a vascular wall given that the vascular wall moves in and out in accordance with a pulse.

5. A system for providing an image of a target region located within an intravascular environment, said system comprising: an imaging apparatus comprising
   a. a camera having at least one light sensing region for detecting light, the sensing region being located within a portion of the apparatus inserted into the intravascular environment;
   b. at least one light source for emitting polarized light to impinge upon said target region, the light source being positioned and oriented along an insertion end of the apparatus so that at least a portion of the light that it emits is reflected by the target region to be detected by the sensing region;
   c. at least one polarization filter for polarization filtering said light, said filter being disposed on the light path such that light reflected from said target region passes through said filter before being detected by said light sensing region; and
   d. the system further comprising a processor and stored instructions for implementing an algorithm for reconstruction of at least one image from light detected by the light sensing region, the reconstruction being based upon the detected polarization filtered light; and wherein the stored instructions for reconstruction of at least one image from light detected by said light sensing region further comprise an algorithm based upon expected light reflection behavior for light emitted within a continuous tubular structure in order to recognize and exclude reflected light that is not expected according to said behavior, wherein the stored instructions for reconstruction include a point illumination model for a continuous tubular structure; and further based upon expected light reflection behavior within a two directional pulse related intravascular fluid movement in order to recognize and exclude reflected light that is expected according to said behavior, wherein the stored instructions for reconstruction include a brightness behavior model for a point moving in a pulsed fluid past a point illumination source.

6. A system for providing an image of a target region located within an intravascular environment, said system comprising: an imaging apparatus comprising
   a. a camera having at least one light sensing region for detecting light, the sensing region being located within a portion of the apparatus inserted into the intravascular environment;
   b. at least one light source for emitting polarized light to impinge upon said target region, the light source being positioned and oriented along an insertion end of the apparatus so that at least a portion of the light that it emits is reflected by the target region to be detected by the sensing region;
   c. at least one polarization filter for polarization filtering said light, said filter being disposed on the light path such that light reflected from said target region passes through said filter before being detected by said light sensing region; and
   d. the system further comprising a processor and stored instructions for implementing an algorithm for reconstruction of at least one image from light detected by the light sensing region, the reconstruction being based upon the detected polarization filtered light; and wherein said at least one light source is controllable to emit said light to impinge upon a predetermined field including said target region and substantially excluding surroundings of said target region, thereby to reduce surrounding-induced reflected light from being detected by said light sensing region; the apparatus further comprising stored instructions for reconstruction of at least one image from light detected by said light sensing region based upon expected light reflection behavior for light emitted within a continuous tubular structure in order to recognize and exclude reflected light that is not expected according to said behavior, wherein the stored instructions for reconstruction include a point illumination model for a continuous tubular structure.

7. A system for providing an image of a target region located within an intravascular environment, said system comprising: an imaging apparatus comprising
   a. a camera having at least one light sensing region for detecting light, the sensing region being located within a portion of the apparatus inserted into the intravascular environment;
   b. at least one light source for emitting polarized light to impinge upon said target region, the light source being positioned and oriented along an insertion end of the apparatus so that at least a portion of the light that it emits is reflected by the target region to be detected by the sensing region;
   c. at least one polarization filter for polarization filtering said light, said filter being disposed on the light path such that light reflected from said target region passes through said filter before being detected by said light sensing region; and
   d. the system further comprising a processor and stored instructions for implementing an algorithm for reconstruction of at least one image from light detected by the light sensing region, the reconstruction being based upon the detected polarization filtered light; and wherein said at least one light source is controllable to emit said light to impinge upon a predetermined field including said target region and substantially excluding surroundings of said target region, thereby to reduce surrounding-induced reflected light from being detected by said light sensing region; the apparatus further comprising stored instructions for reconstruction of at least one image from light detected by said light sensing region based upon expected light reflection behavior within a two directional pulse related intravascular fluid movement in order to recognize and exclude reflected light that is expected according to said behavior, wherein the stored instructions for reconstruction include a brightness behavior model for a point moving in a pulsed fluid past a point illumination source.

8. A system for providing an image of a target region located within an intravascular environment, said system comprising: an imaging apparatus comprising
   a. a camera having at least one light sensing region for detecting light, the sensing region being located within a portion of the apparatus inserted into the intravascular environment;
   b. at least one light source for emitting polarized light to impinge upon said target region, the light source being positioned and oriented along an insertion end of the apparatus so that at least a portion of the light that it emits is reflected by the target region to be detected by the sensing region;
   c. at least one polarization filter for polarization filtering said light, said filter being disposed on the light path such that light reflected from said target region passes through said filter before being detected by said light sensing region; and
   d. the system further comprising a processor and stored instructions for implementing an algorithm for reconstruction of at least one image from light detected by the light sensing region, the reconstruction being based upon the detected polarization filtered light; and
further comprising stored instructions for reconstruction of at least one image from light detected by said light sensing region based upon expected light reflection behavior for light emitted within a continuous tubular structure in order to recognize and exclude reflected light that is not expected according to said behavior, and wherein the stored instructions for reconstruction include a point illumination model for a continuous tubular structure; and further based upon expected light reflection behavior for light emitted within a pulse related radially expanding and contracting vascular vessel in order to recognize and exclude light that is not expected according to said behavior, wherein the stored instructions for reconstruction include a model of brightness variation behavior expected from a vascular wall given that the vascular wall moves in and out in accordance with a pulse.

9. A system for providing an image of a target region located within an intravascular environment, said system comprising: an imaging apparatus comprising
   a. a camera having at least one light sensing region for detecting light, the sensing region being located within a portion of the apparatus inserted into the intravascular environment;
   b. at least one light source for emitting polarized light to impinge upon said target region, the light source being positioned and oriented along an insertion end of the apparatus so that at least a portion of the light that it emits is reflected by the target region to be detected by the sensing region;
   c. at least one polarization filter for polarization filtering said light, said filter being disposed on the light path such that light reflected from said target region passes through said filter before being detected by said light sensing region; and
   d. the system further comprising a processor and stored instructions for implementing an algorithm for reconstruction of at least one image from light detected by the light sensing region, the reconstruction being based upon the detected polarization filtered light; and
further comprising stored instructions for reconstruction of at least one image from light detected by said light sensing region, based upon expected light reflection behavior within a two directional pulse related intravascular fluid movement in order to recognize and exclude reflected light that is expected according to said behavior, wherein the stored instructions for reconstruction include a brightness behavior model for a point moving in a pulsed fluid past a point illumination source; and further based upon expected light reflection behavior for light emitted within a pulse related radially expanding and contracting vascular vessel in order to recognize and exclude light that is not expected according to said behavior, wherein the stored instructions for reconstruction include a model of brightness variation behavior expected from a vascular wall given that the vascular wall moves in and out in accordance with a pulse.

10. A system for providing an image of a target region located within an intravascular environment, said system comprising: an imaging apparatus comprising
   a. a camera having at least one light sensing region for detecting light, the sensing region being located within a portion of the apparatus inserted into the intravascular environment;
   b. at least one light source for emitting polarized light to impinge upon said target region, the light source being positioned and oriented along an insertion end of the apparatus so that at least a portion of the light that it emits is reflected by the target region to be detected by the sensing region;
   c. at least one polarization filter for polarization filtering said light, said filter being disposed on the light path such that light reflected from said target region passes through said filter before being detected by said light sensing region; and
   d. the system further comprising a processor and stored instructions for implementing an algorithm for reconstruction of at least one image from light detected by the light sensing region, the reconstruction being based upon the detected polarization filtered light; and
wherein said at least one light source is controllable to emit said light to impinge upon a predetermined field including said target region and substantially excluding surroundings of said target region, thereby to reduce surrounding-induced reflected light from being detected by said light sensing region, said apparatus further comprising stored instructions for reconstruction of at least one image from light detected by said light sensing region, said reconstruction being based upon expected light reflection behavior for light emitted within a pulse related radially expanding and contracting vascular vessel in order to recognize and exclude light that is not expected according to said behavior, wherein the stored instructions for reconstruction include a model of brightness variation behavior expected from a vascular wall given that the vascular wall moves in and out in accordance with a pulse.

11. A system for providing an image of a target region located within an intravascular environment, said system comprising: an imaging apparatus comprising
   a. a camera having at least one light sensing region for detecting light, the sensing region being located within a portion of the apparatus inserted into the intravascular environment;
   b. at least one light source for emitting polarized light to impinge upon said target region, the light source being positioned and oriented along an insertion end of the apparatus so that at least a portion of the light that it emits is reflected by the target region to be detected by the sensing region;
   c. at least one polarization filter for polarization filtering said light, said filter being disposed on the light path such that light reflected from said target region passes through said filter before being detected by said light sensing region; and d. the system further comprising a processor and stored instructions for implementing an algorithm for reconstruction of at least one image from light detected by the light sensing region, the reconstruction being based upon the detected polarization filtered light; and further comprising stored instructions for reconstruction of at least one image from light detected by said light sensing region based upon expected light reflection behavior for light emitted within a continuous tubular structure in order to recognize and exclude reflected light that is not expected according to said behavior, wherein the stored instructions for reconstruction include a point illumination model for a continuous tubular structure, and further based upon expected light reflection behavior within a two directional pulse related intravascular fluid movement in order to recognize and exclude reflected light that is expected according to said behavior, wherein the stored instructions for reconstruction include a brightness behavior model for a point moving in a pulsed fluid past a point illumination source; and further based upon expected light reflection behavior for light emitted within a pulse related radially expanding and contracting vascular vessel in order to recognize and exclude light that is not expected according to said behavior, wherein the stored instructions for reconstruction include a model of brightness variation behavior expected from a vascular wall given that the vascular wall moves in and out in accordance with a pulse.

12. A system for providing an image of a target region located within an intravascular environment, said system comprising: an imaging apparatus comprising a. a camera having at least one light sensing region for detecting light, the sensing region being located within a portion of the apparatus inserted into the intravascular environment;

b. at least one light source for emitting polarized light to impinge upon said target region, the light source being positioned and oriented along an insertion end of the apparatus so that at least a portion of the light that it emits is reflected by the target region to be detected by the sensing region;

c. at least one polarization filter for polarization filtering said light, said filter being disposed on the light path such that light reflected from said target region passes through said filter before being detected by said light sensing region; and d. the system further comprising a processor and stored instructions for implementing an algorithm for reconstruction of at least one image from light detected by the light sensing region, the reconstruction being based upon the detected polarization filtered light; and wherein said at least one light source is controllable to emit said light to impinge upon a predetermined field including said target region and substantially excluding surroundings of said target region, thereby to reduce surrounding-induced reflected light from being detected by said light sensing region; and further comprising stored instructions for reconstruction of at least one image from light detected by said light sensing region is based upon expected light reflection behavior for light emitted within a continuous tubular structure in order to recognize and exclude reflected light that is not expected according to said behavior, wherein the stored instructions for reconstruction include a point illumination model for a continuous tubular structure; and further based upon expected light reflection behavior for light emitted within a pulse related radially expanding and contracting vascular vessel in order to recognize and exclude light that is not expected according to said behavior, wherein the stored instructions for reconstruction include a model of brightness variation behavior expected from a vascular wall given that the vascular wall moves in and out in accordance with a pulse.

13. A system for providing an image of a target region located within an intravascular environment, said system comprising: an imaging apparatus comprising a. a camera having at least one light sensing region for detecting light, the sensing region being located within a portion of the apparatus inserted into the intravascular environment;

b. at least one light source for emitting polarized light to impinge upon said target region, the light source being positioned and oriented along an insertion end of the apparatus so that at least a portion of the light that it emits is reflected by the target region to be detected by the sensing region;

c. at least one polarization filter for polarization filtering said light, said filter being disposed on the light path such that light reflected from said target region passes through said filter before being detected by said light sensing region; and d. the system further comprising a processor and stored instructions for implementing an algorithm for reconstruction of at least one image from light detected by the light sensing region, the reconstruction being based upon the detected polarization filtered light; and wherein said at least one light source is controllable to emit said light to impinge upon a predetermined field including said target region and substantially excluding surroundings of said target region, thereby to reduce surrounding-induced reflected light from being detected by said light sensing region; and further comprising stored instructions for reconstruction of at least one image from light detected by said light sensing region, said reconstruction being based upon expected light reflection behavior within a two directional pulse related intravascular fluid movement in order to recognize and exclude reflected light that is expected according to said behavior, wherein the stored instructions for reconstruction include a brightness behavior model for a point moving in a pulsed fluid past a point illumination source; and further based upon expected light reflection behavior for light emitted within a pulse related radially expanding and contracting vascular vessel in order to recognize and exclude light that is not expected according to said behavior, wherein the stored instructions for reconstruction include a model of brightness variation behavior expected from a vascular wall given that the vascular wall moves in and out in accordance with a pulse.

14. An apparatus for providing an image of a target region located within an intravascular environment, said apparatus comprising a. a camera having at least one light sensing region for detecting light, and b. at least one light source for emitting light to impinge upon said target region, said light reflected from said target region being detected at said light sensing region; and c. a processor and stored instructions for implementing an algorithm for reconstruction of at least one image from light detected by the light sensing region provided by running an image reconstruction function based upon a point illumination model for a continuous tubular structure, and measuring real-time detected brightness against the model to discriminate between signal and a level of noise from objects other than the object of interest, and excluding the noise.

15. The apparatus of claim 14, wherein said light source is a point source.

16. The apparatus of claim 14, wherein said light source is controllable to emit said light in time sequential flashes.

17. The apparatus of claim 14, wherein said light source is controllable to emit said light in a range of intensities.

18. The apparatus of claim 14, wherein said light source is controllable to emit said light in a range of wavelengths.

19. The apparatus of claim 18, further comprising a shutter located in association with said light sensing region to define a sensing period and operatively associated with the light source to coordinate said sensing period with said predefined emitting period.

20. The apparatus of claim 14, wherein said light source is controllable to emit said light for a predefined period.

21. The apparatus of claim 14, wherein said reconstruction is further based upon expected light reflection behavior within a two directional pulse related intravascular fluid movement in order to recognize and exclude reflected light that is expected according to said behavior, wherein the stored instructions for reconstruction include a brightness behavior model for a point moving in a pulsed fluid past a point illumination source.

22. The apparatus of claim 14, wherein said at least one light source is controllable to emit said light to impinge upon a predetermined field including said target region and substantially excluding surroundings of said target region, thereby to reduce surrounding-induced reflected light from being detected by said light sensing region.

23. The apparatus of claim 14, wherein said reconstruction is further based upon expected light reflection behavior for light emitted within a pulse related radially expanding and contracting vascular vessel in order to recognize and exclude light that is not expected according to said behavior, wherein the stored instructions for reconstruction include a model of brightness variation behavior expected from a vascular wall given that the vascular wall moves in and out in accordance with a pulse.

24. The apparatus of claim 14, wherein said at least one light source is controllable to emit said light to impinge upon a predetermined field including said target region and substantially excluding surroundings of said target region, thereby to reduce surrounding-induced reflected light from being detected by said light sensing region; said reconstruction being further based upon expected light reflection behavior within a two directional pulse related intravascular fluid movement in order to recognize and exclude reflected light that is expected according to said behavior, wherein the stored instructions for reconstruction include a brightness behavior model for a point moving in a pulsed fluid past a point illumination source.

25. The apparatus of claim 14, wherein said at least one light source is controllable to emit said light to impinge upon a predetermined field including said target region and substantially excluding surroundings of said target region, thereby to reduce surrounding-induced reflected light from being detected by said light sensing region; said reconstruction being further based upon expected light reflection behavior within a two directional pulse related intravascular fluid movement in order to recognize and exclude reflected light that is expected according to said behavior, wherein the stored instructions for reconstruction include a brightness behavior model for a point moving in a pulsed fluid past a point illumination source, and further based upon expected light reflection behavior for light emitted within a pulse related radially expanding and contracting vascular vessel in order to recognize and exclude light that is not expected according to said behavior, wherein the stored instructions for reconstruction include a model of brightness variation behavior expected from a vascular wall given that the vascular wall moves in and out in accordance with a pulse.

26. The apparatus of claim 14, wherein said reconstruction is further based upon expected light reflection behavior within a two directional pulse related intravascular fluid movement in order to recognize and exclude reflected light that is expected according to said behavior, wherein the stored instructions for reconstruction include a brightness behavior model for a point moving in a pulsed fluid past a point illumination source, and further based upon expected light reflection behavior for light emitted within a pulse related radially expanding and contracting vascular vessel in order to recognize and exclude light that is not expected according to said behavior, wherein the stored instructions for reconstruction include a model of brightness variation behavior expected from a vascular wall given that the vascular wall moves in and out in accordance with a pulse.

27. The apparatus of claim 14, wherein said at least one light source is controllable to emit said light to impinge upon a predetermined field including said target region and substantially excluding surroundings of said target region, thereby to reduce surrounding-induced reflected light from being detected by said light sensing region, and said reconstruction is further based upon expected light reflection behavior for light emitted within a pulse related radially expanding and contracting vascular vessel in order to recognize and exclude light that is not expected according to said behavior, wherein the stored instructions for reconstruction include a model of brightness variation behavior expected from a vascular wall given that the vascular wall moves in and out in accordance with a pulse.

28. An apparatus for providing an image of a target region located within an intravascular environment, said apparatus comprising:
   a. a camera having at least one light sensing region for detecting light; and
   b. at least one light source for emitting light to impinge upon said target region, said light reflected from said target region being detected by said light sensing region;
   c. a processor and stored instructions for implementing an algorithm for reconstruction of at least one image from light detected by the light sensing region, the reconstruction provided by running an image reconstruction function based upon a brightness behavior model using a point moving in a pulsed fluid past a point illumination source and excluding points that have a level of brightness changes in accordance with that model.

29. The apparatus of claim 28, wherein said light source is a point source.

30. The apparatus of claim 28, wherein said light source is controllable to emit said light in time sequential flashes.

31. The apparatus of claim 28, wherein said light source is controllable to emit said light in a range of intensities.

32. The apparatus of claim 28, wherein said light source is controllable to emit said light in a range of wavelengths.

33. The apparatus of claim 28, wherein said light source is controllable to emit said light for a predefined period.

34. The apparatus of claim 33, further comprising a shutter located in association with said light sensing region to define a sensing period and operatively associated with the light source to coordinate said sensing period with said predefined emitting period.

35. The apparatus of claim 28, wherein said at least one light source is controllable to emit said light to impinge upon a predetermined field including said target region and substantially excluding surroundings of said target region, thereby to reduce surrounding-induced reflected light from being detected by said light sensing region.

36. The apparatus of claim 28, wherein said reconstruction is further based upon expected light reflection behavior for light emitted within a pulse related radially expanding and contracting vascular vessel in order to recognize and exclude light that is not expected according to said behavior, wherein the stored instructions for reconstruction include a model of brightness variation behavior expected from a vascular wall given that the vascular wall moves in and out in accordance with a pulse.

37. The apparatus of claim 28, wherein said at least one light source is controllable to emit said light to impinge upon a predetermined field including said target region and substantially excluding surroundings of said target region, thereby to reduce surrounding-induced reflected light from being detected by said light sensing region, and said reconstruction is further based upon expected light reflection behavior for light emitted within a pulse related radially expanding and contracting vascular vessel in order to recognize and exclude light that is not expected according to said behavior, wherein the stored instructions for reconstruction include a model of brightness variation behavior expected from a vascular wall given that the vascular wall moves in and out in accordance with a pulse.

38. An system for providing an image of a target region located within an intravascular environment, said system comprising an imaging apparatus comprising:
   a. a camera having at least one light sensing region for detecting light; and
   b. at least one light source for emitting light to impinge upon said target region, said light source being controllable to emit said light to impinge upon a predetermined field including said target region and substantially excluding surroundings of said target region, thereby to reduce an amount of reflected light generated by said surroundings from being detected by said light sensing region; and
the system further comprising a processor and stored instructions for reconstruction of at least one image from light detected by said light sensing region, said reconstruction being based upon expected light reflection behavior for light emitted within a pulse related radially expanding and contracting vascular vessel in order to recognize and exclude light that is not expected according to said behavior, wherein the stored instructions include a model of brightness variation behavior expected from a vascular wall given that the vascular wall moves in and out in accordance with a pulse.

39. An apparatus for providing an image of a target region located within an intravascular environment, said apparatus comprising:
   a. a camera having at least one light sensing region for detecting light; and
   b. at least one light source for emitting light to impinge upon said target region, said light reflected from said target region being detected by said light sensing region;
   c. a processor and stored instructions for reconstruction of at least one image from light detected by the light sensing region, the reconstruction provided by running an image reconstruction function based upon a model of brightness variation behavior expected from a vascular wall given that the vascular wall moves in and out in accordance with a pulse.

40. The apparatus of claim 39, wherein said light source is a point source.

41. The apparatus of claim 39, wherein said light source is controllable to emit said light in time sequential flashes.

42. The apparatus of claim 39, wherein said light source is controllable to emit said light in a range of intensities.

43. The apparatus of claim 39, wherein said light source is controllable to emit said light in a range of wavelengths.

44. The apparatus of claim 39, wherein said light source is controllable to emit said light for a predefined period.

45. The apparatus of claim 39, further comprising a shutter located in association with said light sensing region to define a sensing period and operatively associated with the light source to coordinate said sensing period with said predefined emitting period.

46. A method for providing an image of a target region located within an intravascular environment, said method comprising:
   a. inserting an imaging apparatus into said intravascular environment in proximity to said target region;
   b. emitting light from a light source to impinge upon said target region;
   c. detecting said light; and
   d. reconstructing at least one image from said detected light based upon expected light reflection behavior for light emitted within a continuous tubular structure in order to recognize and exclude reflected light that is not expected according to said behavior by running an image reconstruction function based upon a point illumination model used for a continuous tubular structure and measuring real-time detected brightness against the model to discriminate between signal and a level of noise from objects other than the object of interest, and excluding the noise.

47. The method of claim 46, further comprising one or more selected from the group consisting of:
   a. reconstructing at least one image from said detected light based upon expected light reflection behavior within a two directional pulse related intravascular fluid movement in order to recognize and exclude reflected light that is expected according to said behavior by running an image reconstruction function based upon a brightness behavior model using a point moving in a pulsed fluid past a point illumination source and excluding points that have a level of brightness that changes in accordance with that model;
   b. reconstructing at least one image from said detected light based upon expected light reflection behavior for light emitted within a pulse related radially expanding and contracting vascular vessel in order to recognize and exclude light that is not expected according to said behavior by running an image reconstruction function based upon a model of brightness variation behavior expected from a vascular wall given that the vascular wall moves in and out in accordance with a pulse;
   c. emitting said light to impinge upon a predetermined field including said target region and substantially excluding surroundings of said target region, thereby to reduce surrounding-induced reflected light from being detected;
   d. conveying data representing at least one reconstructed image of said target region to a viewable location;
   e. providing for graphical user interfacing including providing at least one graphical control for entering at least one user command and displaying said at least one reconstructed image; and
   f. altering optical properties within said intravascular environment in proximity to said imaging apparatus.

48. The method of claim 46, wherein said intravascular environment is within a vein or an artery and said target region includes the interior wall of said vein or artery and matter in contact with said interior wall.

49. A method for providing an image of a target region located within an intravascular environment, said method comprising:
   a. inserting an imaging apparatus into said intravascular environment in proximity to said target region;
   b. emitting light from a light source to impinge upon said target region;
   c. detecting said light; and
   d. reconstructing at least one image from said detected light based upon expected light reflection behavior within a two directional pulse related intravascular fluid movement in order to recognize and exclude reflected light that is expected according to said behavior by running an image reconstruction function based upon a brightness behavior model using a point moving in a pulsed fluid past a point illumination source and excluding points that have a level of brightness that changes in accordance with that model.

50. The method of claim 49, further comprising one or more selected from the group consisting of:
   a. reconstructing at least one image from said detected light based upon expected light reflection behavior for light emitted within a pulse related radially expanding and contracting vascular vessel in order to recognize and exclude light that is not expected according to said behavior by running an image reconstruction function based upon a model of brightness variation behavior expected from a vascular wall given that the vascular wall moves in and out in accordance with a pulse;
   b. emitting said light to impinge upon a predetermined field including said target region and substantially excluding surroundings of said target region, thereby to reduce surrounding-induced reflected light from being detected;
   d. conveying data representing at least one reconstructed image of said target region to a viewable location;
   e. providing for graphical user interfacing including providing at least one graphical control for entering at least one user command and displaying said at least one reconstructed image; and
   f. altering optical properties within said intravascular environment in proximity to said imaging apparatus.

51. The method of claim 49, wherein said intravascular environment is within a vein or an artery and said target region includes the interior wall of said vein or artery and matter in contact with said interior wall.

52. A method for providing an image of a target region located within an intravascular environment, said method comprising:
   a. inserting an imaging apparatus into said intravascular environment in proximity to said target region;
   b. emitting light from a light source to impinge upon said target region;
   c. detecting said light; and
   d. reconstructing at least one image from said detected light based upon expected light reflection behavior for light emitted within a pulse related radially expanding and contracting vascular vessel in order to recognize and exclude light that is not expected according to said behavior by running an image reconstruction function based upon a model of brightness variation behavior expected from a vascular wall given that the vascular wall moves in and out in accordance with a pulse.

53. The method of claim 52, further comprising one or more selected from the group consisting of:
   a. emitting said light to impinge upon a predetermined field including said target region and substantially excluding surroundings of said target region, thereby to reduce surrounding-induced reflected light from being detected;
   a. conveying data representing at least one reconstructed image of said target region to a viewable location;
   b. providing for graphical user interfacing including providing at least one graphical control for entering at least one user command and displaying said at least one reconstructed image; and
   d. altering optical properties within said intravascular environment in proximity to said imaging apparatus.

54. The method of claim 52, wherein said intravascular environment is within a vein or an artery and said target region includes the interior wall of said vein or artery and matter in contact with said interior wall.

55. An endoscope system, comprising:
   an elongate body with an insertion portion sized and shaped to fit within the tubular structure of a vascular vessel of a patient's body;
   a camera comprising a sensing region disposed at the distal end of the insertion portion;
   at least one light source for emitting polarized light disposed at the distal end of the insertion portion;
   a polarization filter for polarization filtering of light emitted from the light source and reflected from the vessel's walls or from an object connected to or adjacent the wall;
   wherein the camera, light source and polarization filter are compactly arranged so that light emitted from the light source is reflected off the interior vessel wall and follows at least in part a light path to the sensing region that is substantially perpendicular to the vessel wall, the polarization filter being arranged so that light reflected from the vessel interior walls first passes through the polarization filter before reaching the sensing region; and
   a processing system in communication with the sensing region, comprising a processor and set of stored instructions for reconstructing an image from a signal derived from the sensing region, the set of instructions implementing an algorithm for expected light reflection behavior for light emitted within a continuous tubular structure in order to recognize and exclude light that is not based on expected behavior and wherein the stored instructions include an algorithm implementing a point illumination model for a continuous tubular structure.

56. The endoscope system of claim 55 wherein intravascularly the sensing region is positioned longitudinally along the elongate body.

57. The endoscope system of claim 55 further comprising a channel in the insertion portion for communicating fluid from a fluid source to an area of the vessel surrounding the camera.

58. The endoscope system of claim 55 wherein said sensing region comprises two light sensing regions; said at least one light source comprises two separate light sources, said two light sources being for respectively emitting light for detection by said two light sensing regions; and said at least one polarization filter comprises two separate polarization filters, each of which is associated with one of the sensing regions to filter light prior to detection by the respective sensing region.

* * * * *